(12) United States Patent
Martin et al.

(10) Patent No.: US 10,987,033 B2
(45) Date of Patent: Apr. 27, 2021

(54) AQUEOUS HUMOR MONITORING DEVICES AND METHODS

(71) Applicant: MicroOptx Inc., Maple Grove, MN (US)

(72) Inventors: Roy Christian Martin, Maple Grove, MN (US); Christopher Clark Pulling, Dayton, MN (US); Christopher Thomas Martin, Maple Grove, MN (US); J. David Brown, St. Paul, MN (US)

(73) Assignee: MicroOptx Inc., Maple Grove, MN (US)

( * ) Notice: Subject to any disclaimer, the term of this patent is extended or adjusted under 35 U.S.C. 154(b) by 326 days.

(21) Appl. No.: 15/775,254

(22) PCT Filed: Nov. 11, 2016

(86) PCT No.: PCT/US2016/061477
§ 371 (c)(1),
(2) Date: May 10, 2018

(87) PCT Pub. No.: WO2017/083610
PCT Pub. Date: May 18, 2017

(65) Prior Publication Data
US 2018/0333085 A1    Nov. 22, 2018

Related U.S. Application Data

(60) Provisional application No. 62/253,943, filed on Nov. 11, 2015, provisional application No. 62/407,716, filed on Oct. 13, 2016.

(51) Int. Cl.
*A61B 5/1455*    (2006.01)
*A61B 5/145*    (2006.01)
(Continued)

(52) U.S. Cl.
CPC ........ *A61B 5/14532* (2013.01); *A61B 5/1455* (2013.01); *A61B 5/1459* (2013.01);
(Continued)

(58) Field of Classification Search
None
See application file for complete search history.

(56) References Cited

U.S. PATENT DOCUMENTS

| 6,120,460 A | 9/2000 | Abreu |
| 6,181,957 B1 | 1/2001 | Lambert et al. |

(Continued)

FOREIGN PATENT DOCUMENTS

| CN | 1229345 | 9/1999 |
| CN | 1432139 | 7/2003 |
| WO | WO 2014/164569 | 10/2014 |

OTHER PUBLICATIONS

Extended European Search Report in European Appliction No. 16865059.6 dated Jul. 3, 2019, 84 pages.
(Continued)

*Primary Examiner* — Marjan Fardanesh
(74) *Attorney, Agent, or Firm* — Fish & Richardson P.C.

(57) ABSTRACT

A method for monitoring glucose concentration in aqueous humor can include inserting an implantable device into an eye and determining glucose concentration as a function of glucose sensed at the implantable device. The method can optionally include optically detecting glucose concentration as a function of polarimetry and/or fluorescence. A system for monitoring glucose concentration can include devices described herein.

24 Claims, 24 Drawing Sheets

(51) Int. Cl.
    *A61B 5/1459*     (2006.01)
    *A61B 5/00*     (2006.01)

(52) U.S. Cl.
    CPC .......... *A61B 5/14507* (2013.01); *A61B 5/686* (2013.01); *A61B 5/6821* (2013.01)

(56) References Cited

U.S. PATENT DOCUMENTS

| | | | |
|---|---|---|---|
| 6,442,410 | B1 | 8/2002 | Steffes |
| 6,881,198 | B2 | 4/2005 | Brown |
| 7,245,952 | B2 | 7/2007 | Cameron |
| 7,618,142 | B2 | 11/2009 | Back |
| 7,653,424 | B2 | 1/2010 | March |
| 8,380,270 | B2 | 2/2013 | Menon |
| 2003/0045783 | A1 | 3/2003 | March et al. |
| 2005/0154269 | A1* | 7/2005 | Cameron ........... A61B 5/14555 600/319 |
| 2006/0183986 | A1 | 8/2006 | Rice et al. |
| 2007/0004975 | A1 | 1/2007 | Zribi et al. |
| 2010/0113901 | A1 | 5/2010 | Zhang |
| 2012/0245444 | A1 | 9/2012 | Otis et al. |
| 2013/0090534 | A1 | 4/2013 | Burns et al. |
| 2014/0275923 | A1 | 9/2014 | Haffner et al. |
| 2014/0296674 | A1 | 10/2014 | Etzikorn |
| 2014/0343387 | A1 | 11/2014 | Pugh et al. |

OTHER PUBLICATIONS

International Search Report in International Application No. PCT/US2016/061477 dated Mar. 8, 2017, 4 pages.
McNichols et al., "Development of a Non-invasive Polarimetric Glucose Sensor," IEEE Photonics Society [online] Apr. 1998 [retrieved on Oct. 20, 2015]. Retrieved from the Internet:<URL:http://photonicssociety.org/newsletters/apr98/glucosesensor.htm>, 3 pages.

* cited by examiner

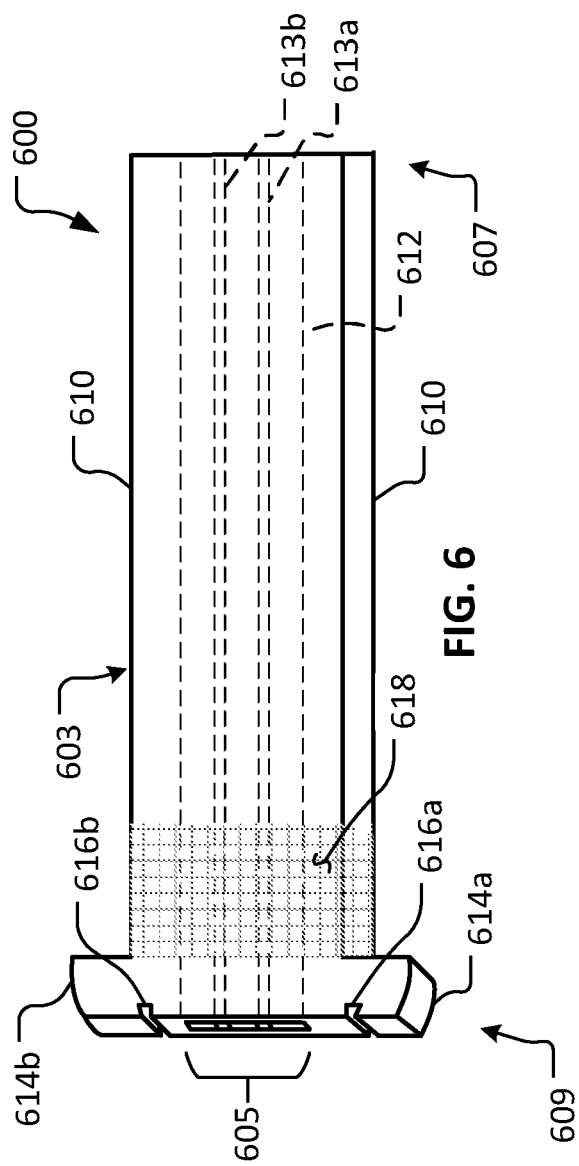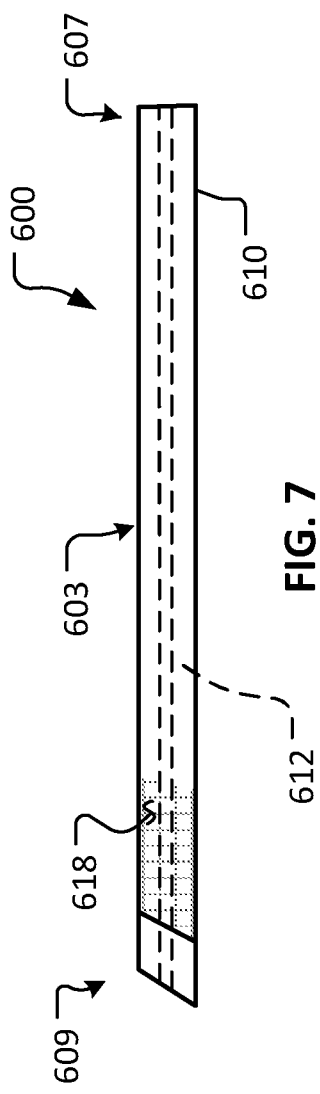

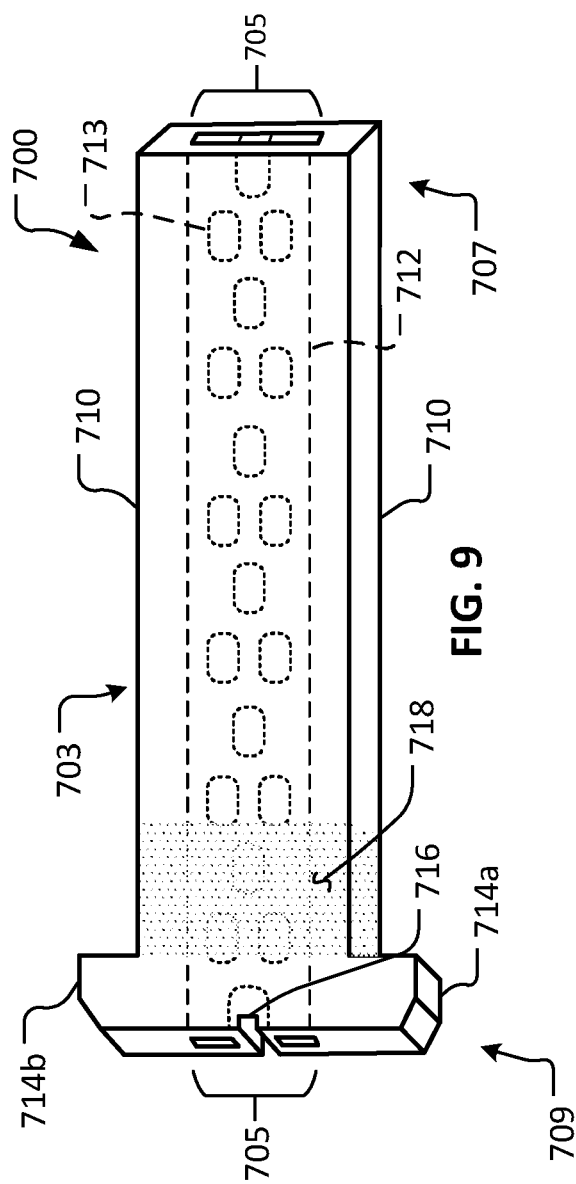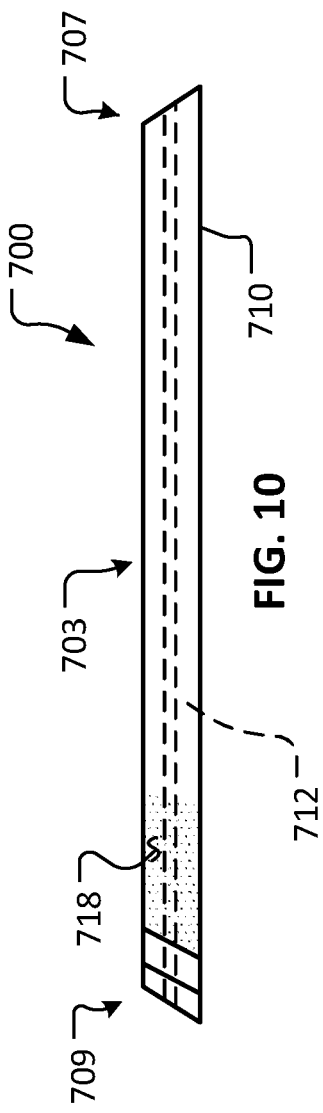
FIG. 9
FIG. 10

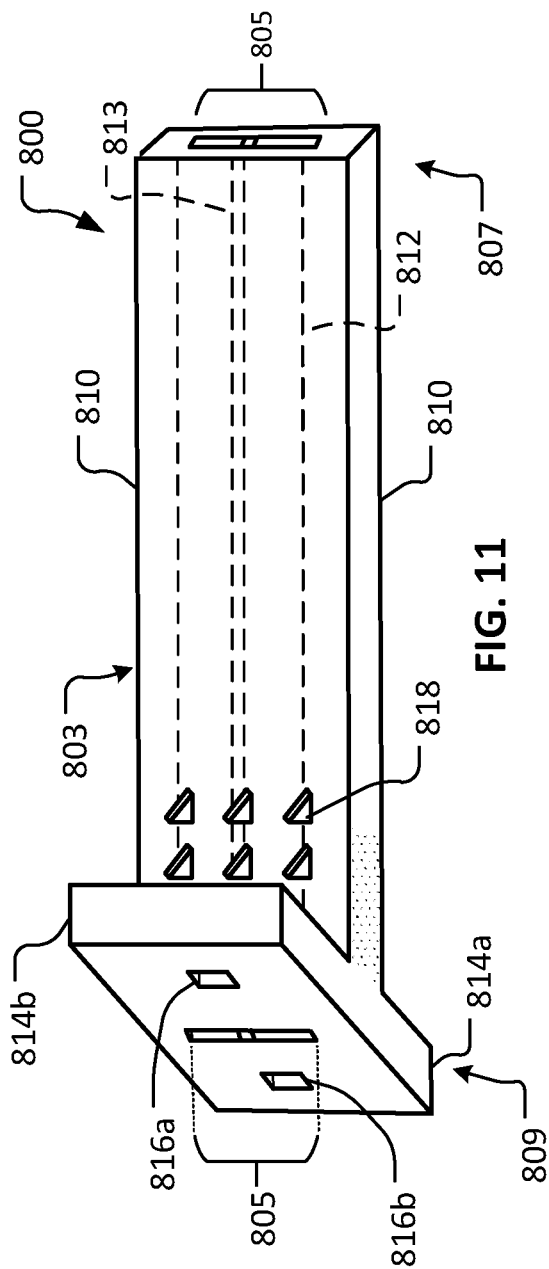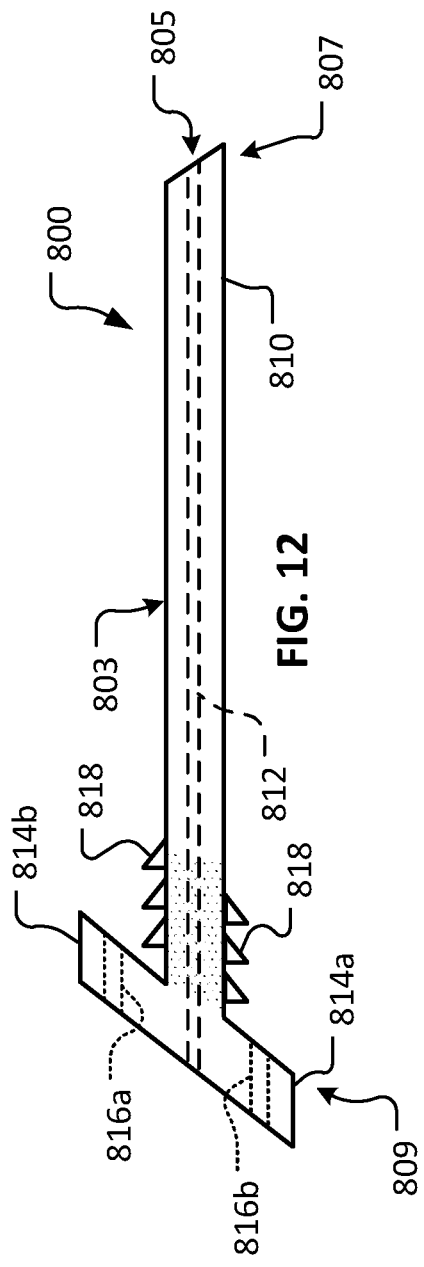

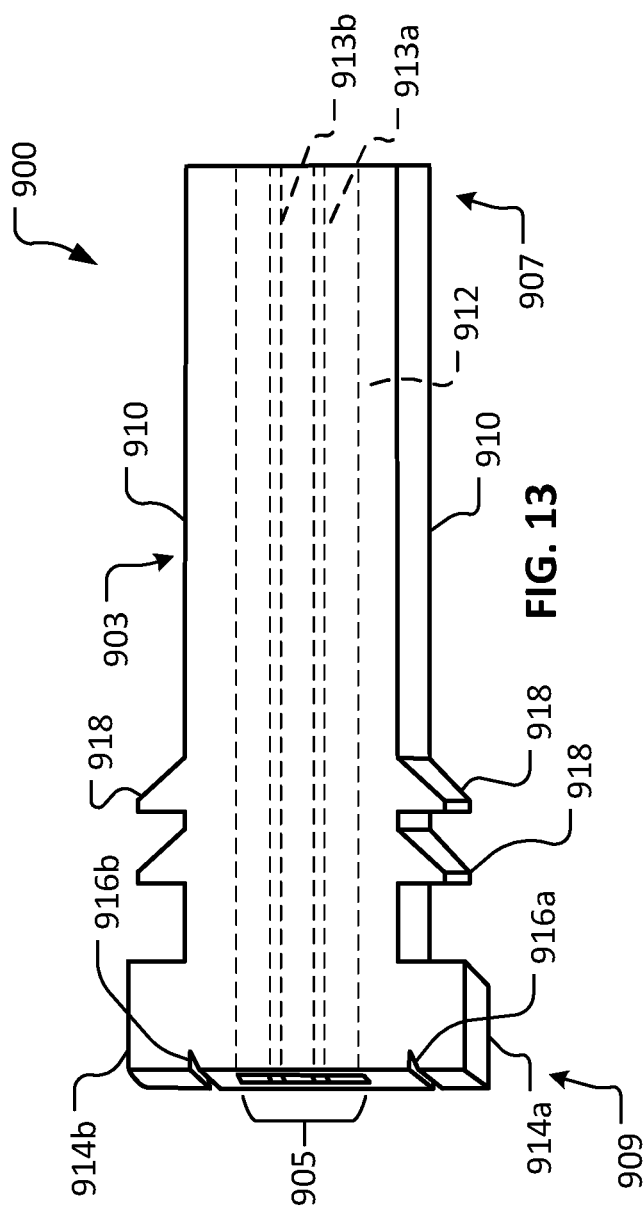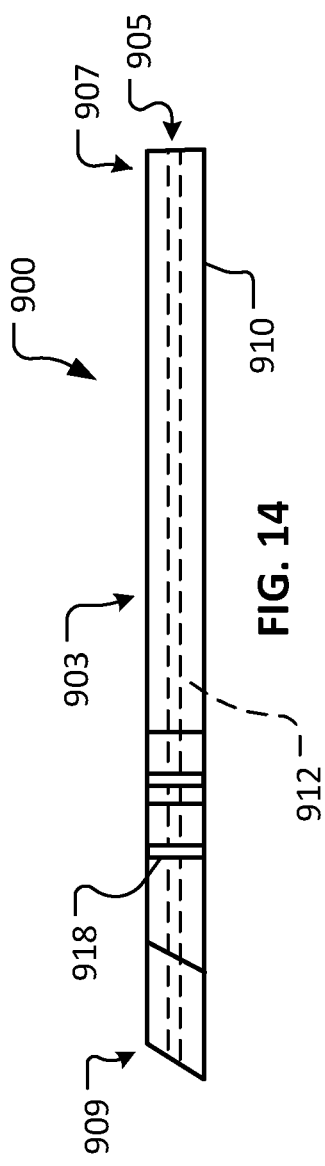

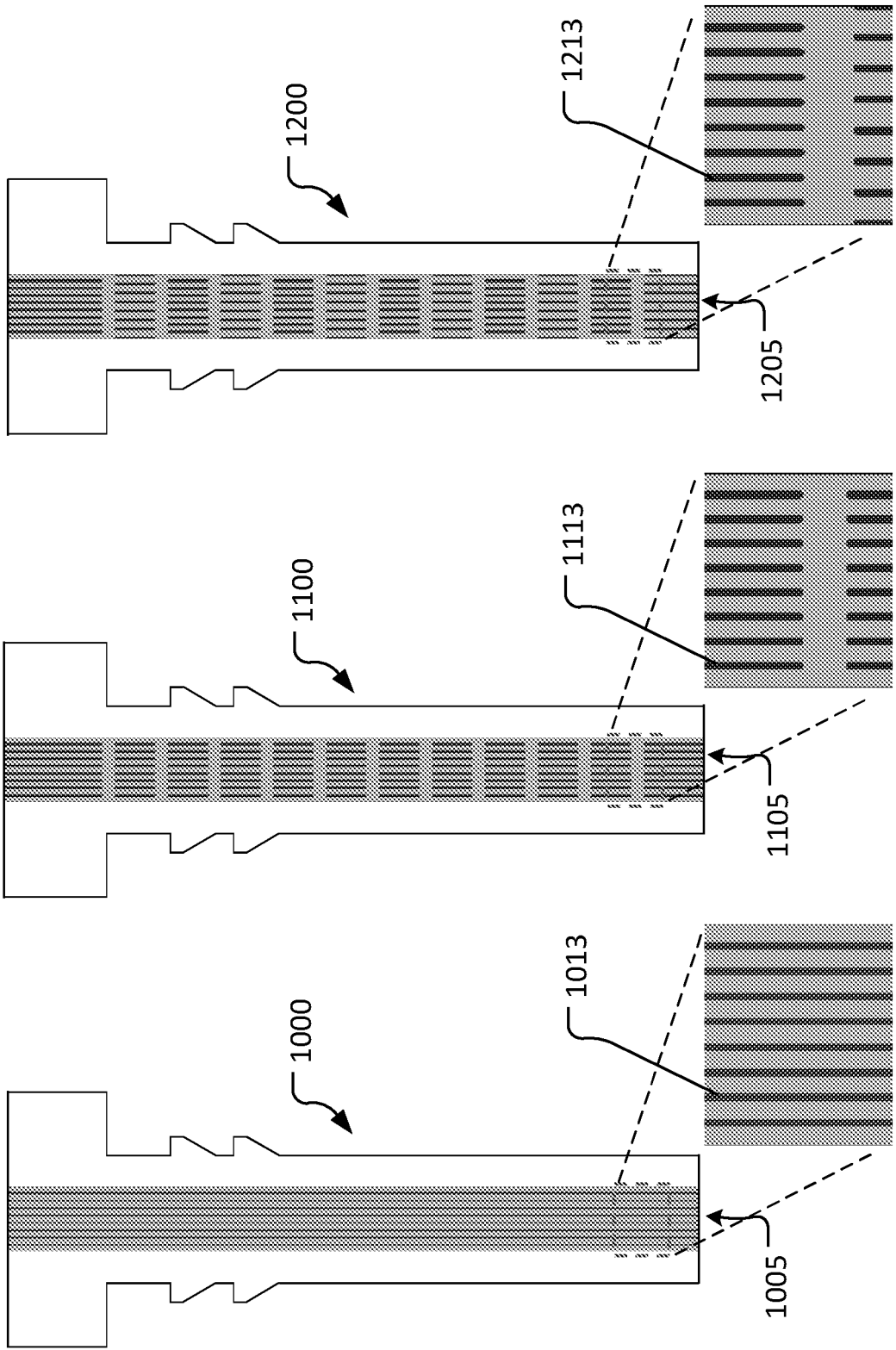

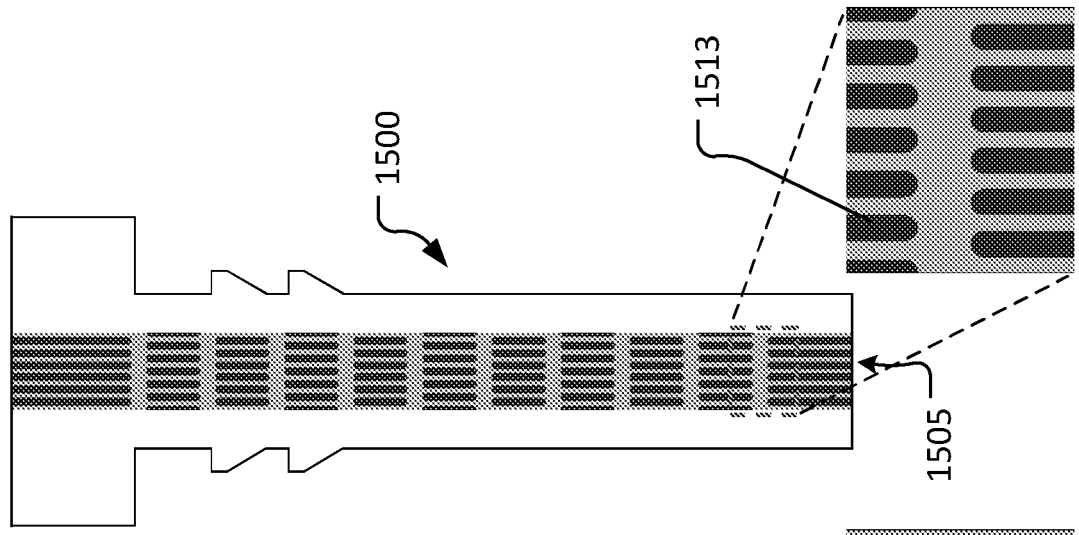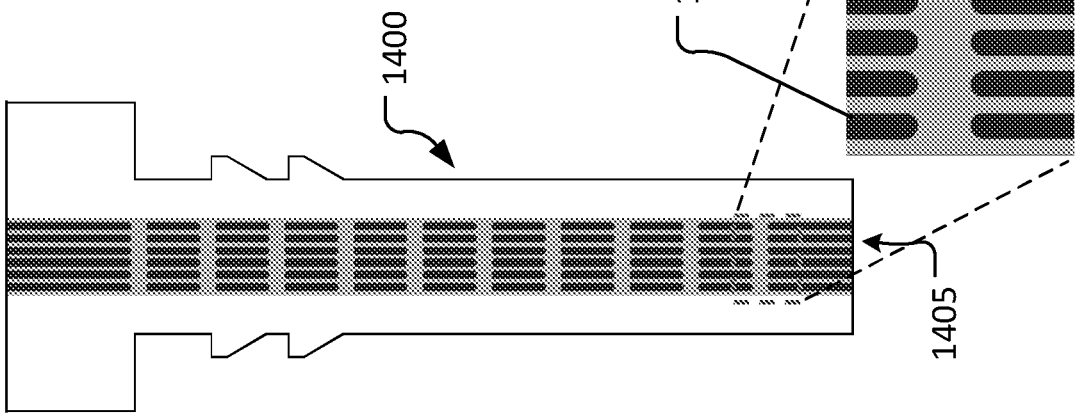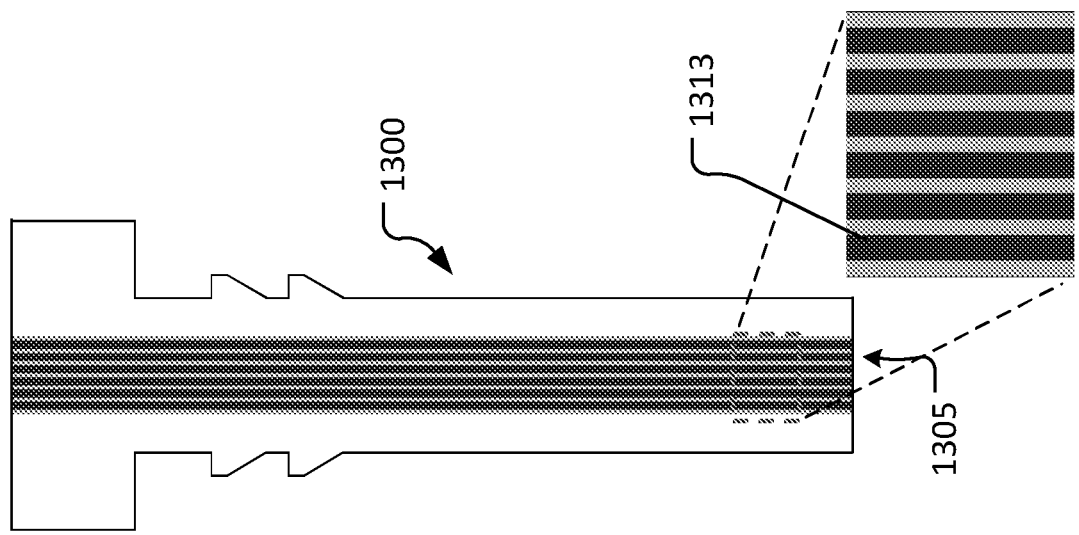

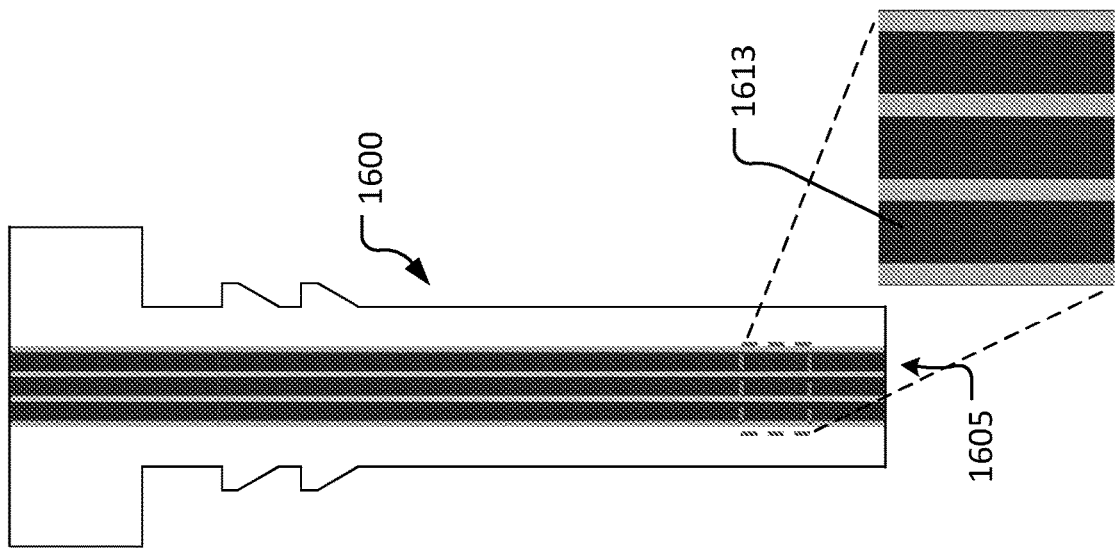
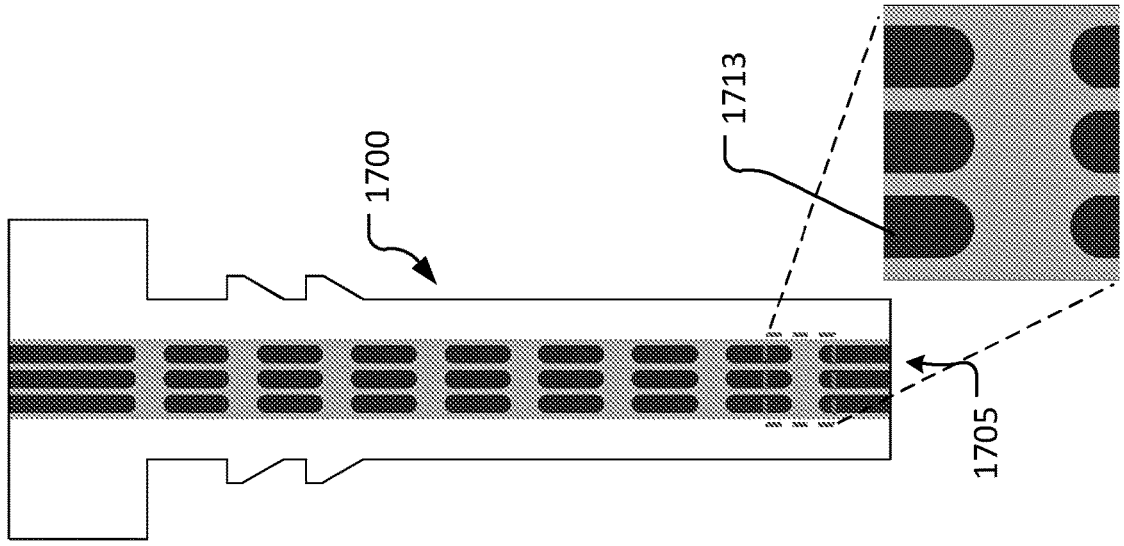
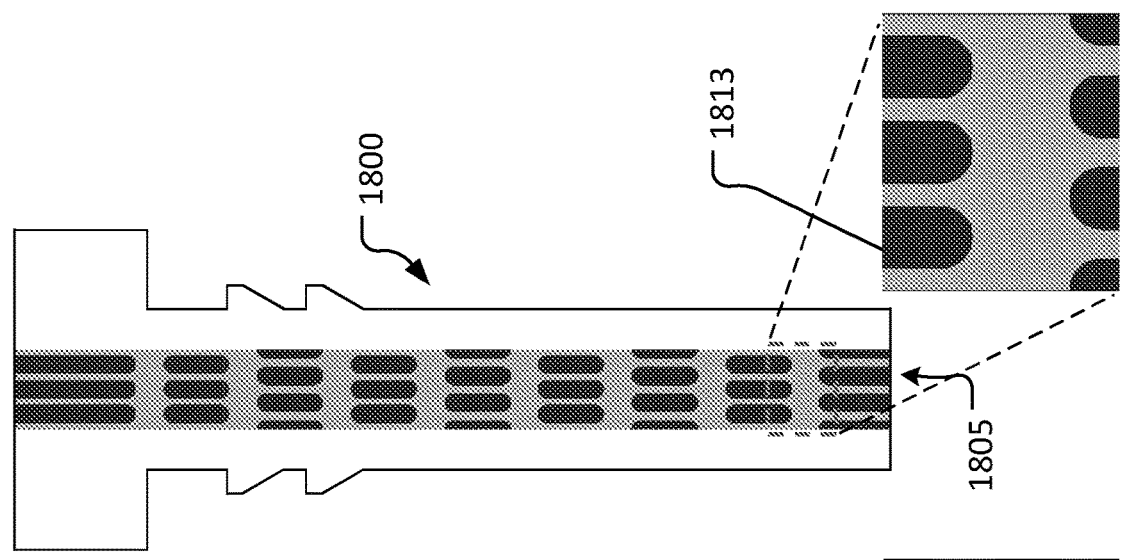

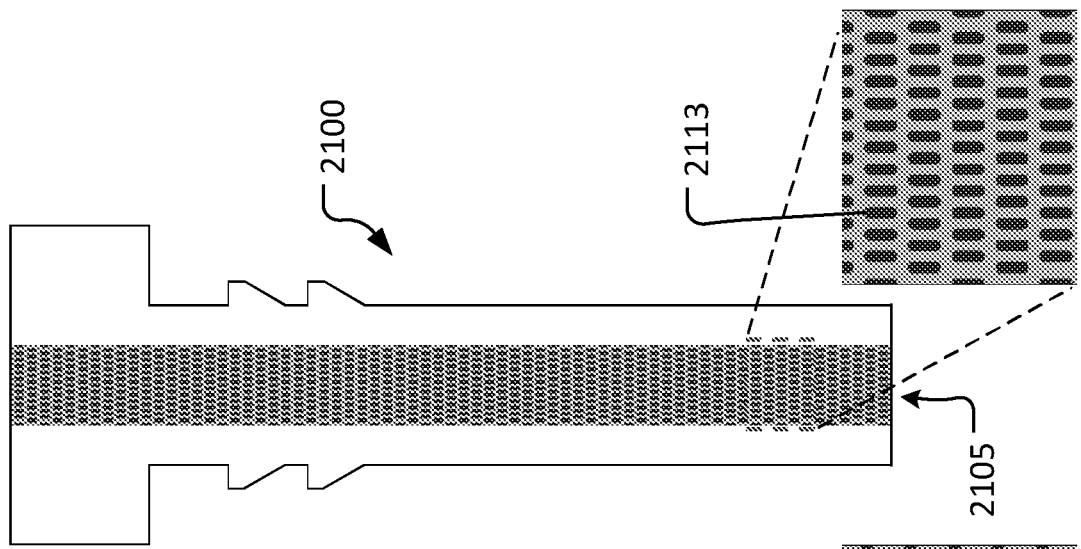
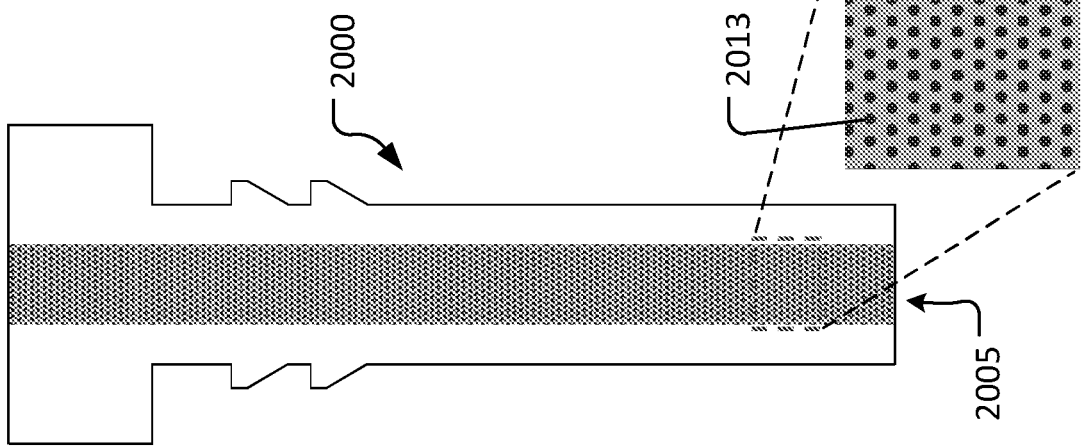
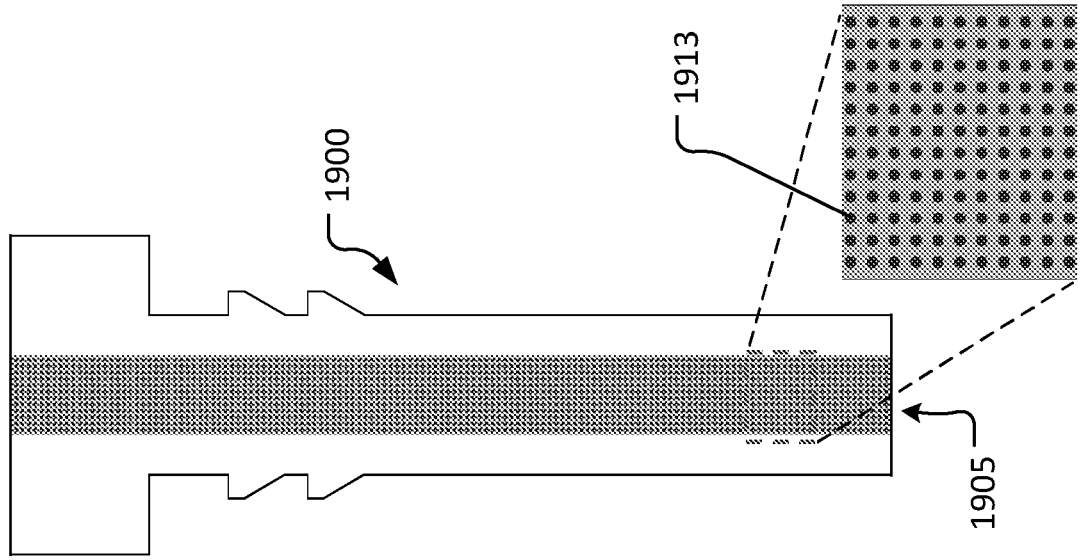

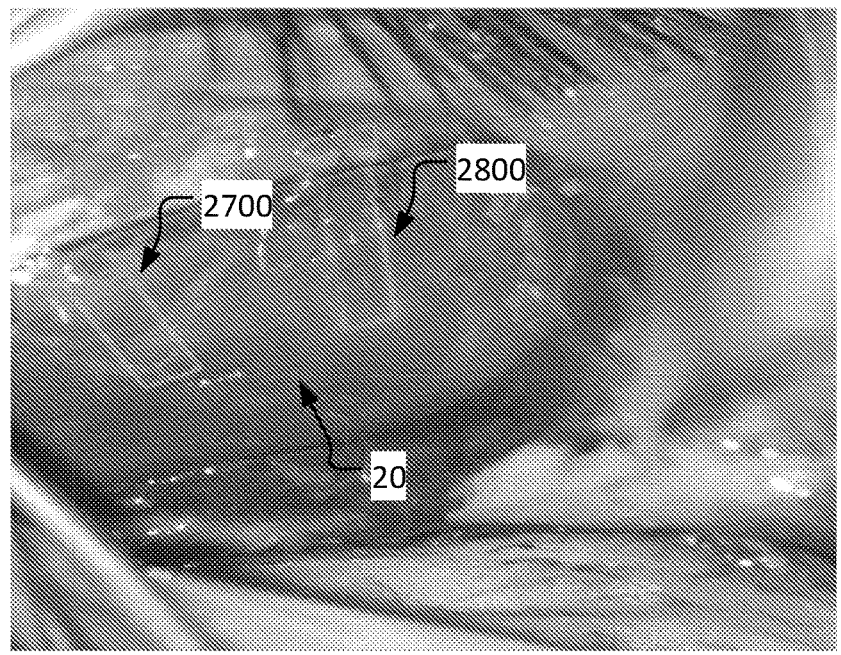
FIG. 34
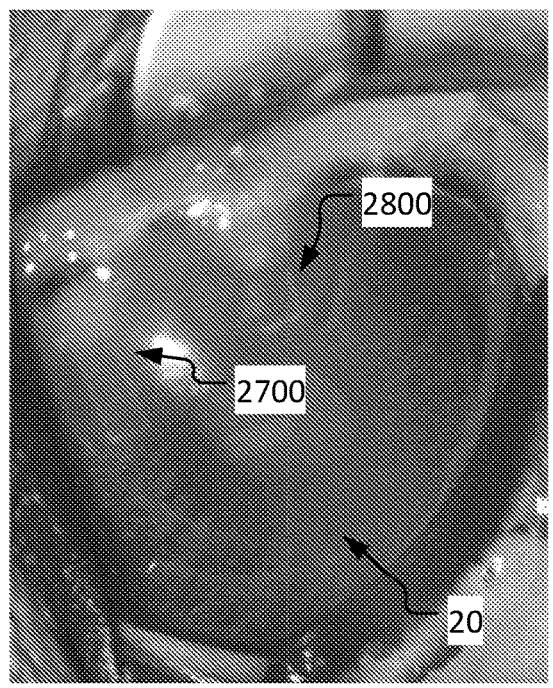 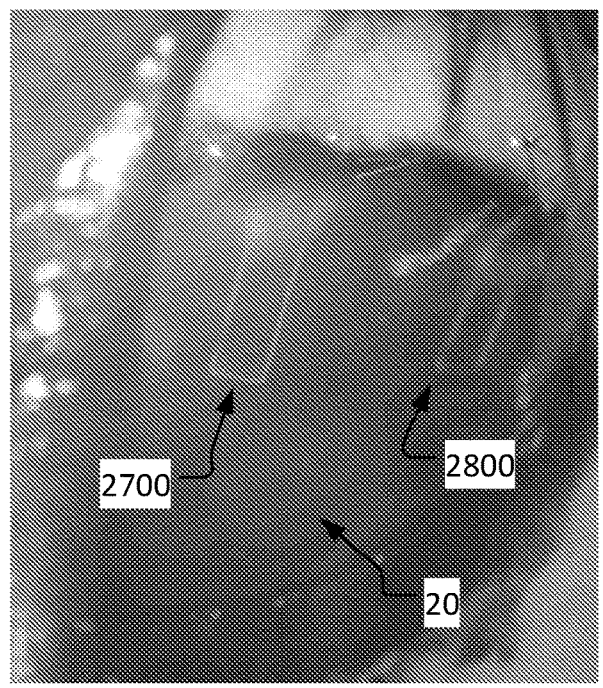
FIG. 35  FIG. 36

AQUEOUS HUMOR MONITORING DEVICES AND METHODS

CROSS REFERENCE TO RELATED APPLICATIONS

This application is a National Stage Application under 35 U.S.C. § 371 and claims the benefit of International Application No. PCT/US2016/061477, filed Nov. 11, 2016, which claims the benefit of U.S. Provisional Application No. 62/253,943, filed Nov. 11, 2015, and U.S. Provisional Application No. 62/407,716, filed Oct. 13, 2016. The disclosures of the prior applications are considered part of and are incorporated by reference in the disclosure of this application.

BACKGROUND

1. Technical Field

This document relates to monitoring of aqueous humor of the eye.

2. Background Information

Aqueous humor is a transparent, gelatinous fluid similar to plasma, but can contain low protein concentrations. Aqueous humor can be secreted from the ciliary epithelium, a structure supporting the lens of the eye. Aqueous humor can be located in the anterior and posterior chambers of the eye, the space between the lens and the cornea.

SUMMARY

This document provides devices and methods for the monitoring of glucose and/or other analyte concentrations in aqueous humor. For example, glucose concentration can be determined as a function of polarimetry and/or fluorescence in conjunction with an implanted device in the eye. The implanted device can also be used to treat conditions such as glaucoma and/or dry eye. Implementations can include any, all, or none of the following features.

In one aspect, a system for monitoring glucose concentration in aqueous humor can include an implantable device and a polarimeter. The implantable device can be configured to be surgically implanted in an eye and have a lumen extending through the implantable device configured to transmit aqueous humor from an interior portion of the eye to an exterior of the eye. The polarimeter can be configured for detecting polarity of the aqueous humor at the implantable device while the implantable device is implanted in the eye and determining glucose concentration as a function of polarity of the aqueous humor at the implantable device while the implantable device is implanted in the eye.

Implementations can include any, all, or none of the following features. The implantable device is open from a first end of the lumen to a second end of the lumen and is configured to maintain a desired intraocular pressure for the treatment of glaucoma. A light source has a polarizer configured to direct a polarized beam of light on the implantable device for detecting glucose concentration in the aqueous humor. The light source is configured to direct the polarized beam of light on a portion of the implantable device that is exterior to the eye such that the polarized beam of light is reflected to the polarimeter in a manner suitable for detection and analysis of polarity of the aqueous humor. The light source is configured to direct the polarized beam of light on a portion of the implantable device that is interior to the eye such that the polarized beam of light passes into the eye and is reflected by the implantable device to the polarimeter in a manner suitable for detection and analysis of polarity of the aqueous humor.

In one aspect, a system for monitoring glucose concentration in aqueous humor can include an implantable device. The implantable device can be configured to be surgically implanted in an eye and have a sensor positioned on a portion of the implantable device so as to be positioned in aqueous humor of the eye when the implantable device is implanted in the eye. A lumen can extend through the implantable device so as to transmit aqueous humor from an interior portion of the eye to an exterior of the eye.

Implementations can include any, all, or none of the following features. An analysis system can be in communication with the sensor and configured for processing data corresponding to sensed glucose concentration by the sensor. The implantable device and the analysis system each include antenna for wirelessly communicating data corresponding to sensed glucose concentration from the analysis system. The sensor comprises a florescence glucose biosensor that relays glucose concentration in aqueous humor via fluorescence. The analysis system comprises an optical detector.

In one aspect, a method can monitor glucose concentration in aqueous humor. The method includes inserting an implantable device into an eye and positioning the implantable device such that a glucose sensor on the implantable device is positioned proximate aqueous humor of the eye.

Implementations can include any, all, or none of the following features. The implantable device has a lumen extending through the implantable device that is configured to transmit aqueous humor from an interior portion of the eye to an exterior of the eye. Fluorescence can be detected via the glucose sensor to determine glucose concentration in aqueous humor in the eye.

In one aspect, a method can monitor glucose concentration in aqueous humor. The method can include providing light to a device implanted in an eye, passing the light through aqueous humor, reflecting the light to an optical detector, and determining glucose concentration in the aqueous humor as a function of the light received at the optical detector. The device can have a lumen extending through the implantable device that is configured to transmit aqueous humor from an interior portion of the eye to an exterior of the eye.

Implementations can include any, all, or none of the following features. The light is projected from a light source having a polarizer and glucose concentration is determined by a polarimeter as a function of polarimetry. The light source directs a polarized beam of light on a portion of the implantable device that is interior to the eye such that the polarized beam of light passes into the eye and is reflected by the implantable device to the polarimeter in a manner suitable for detection and analysis of polarity of the aqueous humor. The light source directs a polarized beam of light on a portion of the implantable device that is exterior to the eye such that the polarized beam of light is reflected to the polarimeter in a manner suitable for detection and analysis of polarity of the aqueous humor exterior to the eye. The implantable device comprises a fluorescent biosensor positioned on a portion of the implantable device in communication with aqueous humor within the eye. Glucose concentration is determined as a function of fluorescence.

In one aspect, a system for monitoring glucose concentration in aqueous humor includes an implantable device configured to be surgically implanted in an eye and a contact lens configured to be worn on the exterior of the eye. The implantable device defines a lumen extending through the implantable device configured to transmit aqueous humor from an interior portion of the eye to an exterior of the eye. The contact lens includes a sensor coupled thereto. The sensor is responsive to the glucose concentration of aqueous humor transmitted through the lumen to the exterior of the eye.

Implementations can include any, all, or none of the following features. The contact lens may further comprise an antenna for wirelessly transmitting signals from the sensor to an external device. The system may include the external device which can be a smart phone or an infusion pump. The sensor may be an electrochemical sensor. The contact lens may include a ballast region that is more weighty than other portions of the contact lens. The contact lens may include a well configured for receiving the aqueous humor transmitted through the lumen to the exterior of the eye. The contact lens may include a ballast region that is more weighty than other portions of the contact lens, and the ballast region may be on an opposite side of the contact lens in relation to the well.

In one aspect, a system for monitoring glucose concentration in aqueous humor includes: an implantable device configured to be surgically implanted in an eye and an analysis system separate from the implantable device. At least a portion of the implantable device includes a fluorescent dye that is responsive to the glucose concentration in the aqueous humor. The analysis system includes a detector configured and operable to detect color or fluorescence of the fluorescent dye. The analysis system is configured to convert signals from the detector to quantified glucose concentration readings.

Implementations can include any, all, or none of the following features. The implantable device may define a lumen extending through the implantable device configured to transmit aqueous humor from an interior portion of the eye to an exterior of the eye. The dye may be at least partially located on an end portion of the implantable device that is external to the eye while the implantable device is implanted in the eye. The dye may be exclusively located on an end portion of the implantable device that is external to the eye while the implantable device is implanted in the eye. In some embodiments, the implantable device does not define a lumen configured to transmit aqueous humor from an interior portion of the eye to an exterior of the eye.

In one aspect, a method for monitoring glucose concentration in aqueous humor includes implanting an implantable device in an eye and providing a contact lens configured to be worn on the exterior of the eye. The contact lens includes a sensor coupled thereto. The implantable device defines a lumen extending through the implantable device configured to transmit aqueous humor from an interior portion of the eye to an exterior of the eye. The sensor is responsive to the glucose concentration of aqueous humor transmitted through the lumen to the exterior of the eye.

In one aspect, a method for monitoring glucose concentration in aqueous humor includes implanting an implantable device in an eye and providing an analysis system separate from the implantable device. At least a portion of the implantable device includes a fluorescent dye that is responsive to the glucose concentration in the aqueous humor. The analysis system includes a detector configured and operable to detect color or fluorescence of the fluorescent dye. The analysis system is configured to convert signals from the detector to quantified glucose concentration readings.

Implementations of the methods can include any, all, or none of the following features. The implantable device may define a lumen extending through the implantable device configured to transmit aqueous humor from an interior portion of the eye to an exterior of the eye. The dye may be at least partially located on an end portion of the implantable device that is external to the eye while the implantable device is implanted in the eye. In some embodiments, the implantable device does not define a lumen configured to transmit aqueous humor from an interior portion of the eye to an exterior of the eye.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 6 is a perspective view of another example device in accordance with some embodiments.

FIG. 7 is a side view of the device of FIG. 6.

FIG. 9 is a perspective view of another example device in accordance with some embodiments.

FIG. 10 is a side view of the device of FIG. 9.

FIG. 11 is a perspective view of another example device in accordance with some embodiments.

FIG. 12 is a side view of the device of FIG. 11.

FIG. 13 is a perspective view of another example device in accordance with some embodiments.

FIG. 14 is a side view of the device of FIG. 13.

FIG. 15 is a plan view of another example device in accordance with some embodiments. An enlarged view of a portion of the lumenal structure is illustrated.

FIG. 16 is a plan view of another example device in accordance with some embodiments. An enlarged view of a portion of the lumenal structure is illustrated.

FIG. 17 is a plan view of another example device in accordance with some embodiments. An enlarged view of a portion of the lumenal structure is illustrated.

FIG. 18 is a plan view of another example device in accordance with some embodiments. An enlarged view of a portion of the lumenal structure is illustrated.

FIG. 19 is a plan view of another example device in accordance with some embodiments. An enlarged view of a portion of the lumenal structure is illustrated.

FIG. 20 is a plan view of another example device in accordance with some embodiments. An enlarged view of a portion of the lumenal structure is illustrated.

FIG. 21 is a plan view of another example device in accordance with some embodiments. An enlarged view of a portion of the lumenal structure is illustrated.

FIG. 22 is a plan view of another example device in accordance with some embodiments. An enlarged view of a portion of the lumenal structure is illustrated.

FIG. 23 is a plan view of another example device in accordance with some embodiments. An enlarged view of a portion of the lumenal structure is illustrated.

FIG. 24 is a plan view of another example device in accordance with some embodiments. An enlarged view of a portion of the lumenal structure is illustrated.

FIG. 25 is a plan view of another example device in accordance with some embodiments. An enlarged view of a portion of the lumenal structure is illustrated.

FIG. 26 is a plan view of another example device in accordance with some embodiments. An enlarged view of a portion of the lumenal structure is illustrated.

FIG. 34 is a photograph of an example eye shortly after receiving an implantation of two devices in accordance with some embodiments.

FIG. 35 is a photograph of the eye of FIG. 34 two weeks after the implantation.

FIG. 36 is a photograph of the eye of FIG. 34 one month after the implantation.

Like reference numbers represent corresponding parts throughout.

DETAILED DESCRIPTION

This document provides devices and methods for monitoring and/or treatment of an eye. For example, this document provides devices configured for implantation into the sclera of an afflicted eye to allow aqueous humor to flow from the anterior chamber of the afflicted eye through a lumen of the device and into the tear film, as well as methods for using such devices to treat a dry eye condition, glaucoma, or another condition. By the strategic selection of particular materials of construction, and/or by controlling the shape and size of the lumen, in some embodiments, a device provided herein can be filterless, or can be designed to include a filter. A filterless eye treatment device described herein, or an eye treatment device having a filter as described herein, can be designed to prevent bacterial ingress and to provide a desired level of outflow resistance to achieve a desired intraocular pressure (typically a low to normal, or slightly above normal intraocular pressure) and a desired moisture level in patients with a dry eye or glaucoma condition. The flow of aqueous humor from the anterior chamber also provides moisture and lubrication to the surface of the eye to alleviate the dry eye symptoms.

Ocular surface diseases (disorders of the surface of the cornea) can be treated using the devices and techniques provided herein. For example any appropriate glaucoma or dry eye condition can be treated using the methods and devices provided herein. For example, dry eye conditions such as, but not limited to, aqueous tear-deficient dry eye, evaporative dry eye, and the like, can be treated using the methods and devices provided herein.

In some embodiments, aqueous humor (also called aqueous humour) can be monitored in conjunction with an implantable device. For example, glucose levels can be monitored in the aqueous humor using techniques involving polarimetry and/or fluorescence. In some embodiments, monitoring of aqueous humor can be performed with a device also configured for treating glaucoma. In some embodiments, monitoring of aqueous humor can be performed with a device also configured for treating dry eye. In some embodiments, monitoring of aqueous humor can be performed with a device not necessarily treating either glaucoma or dry eye.

Figure 1:
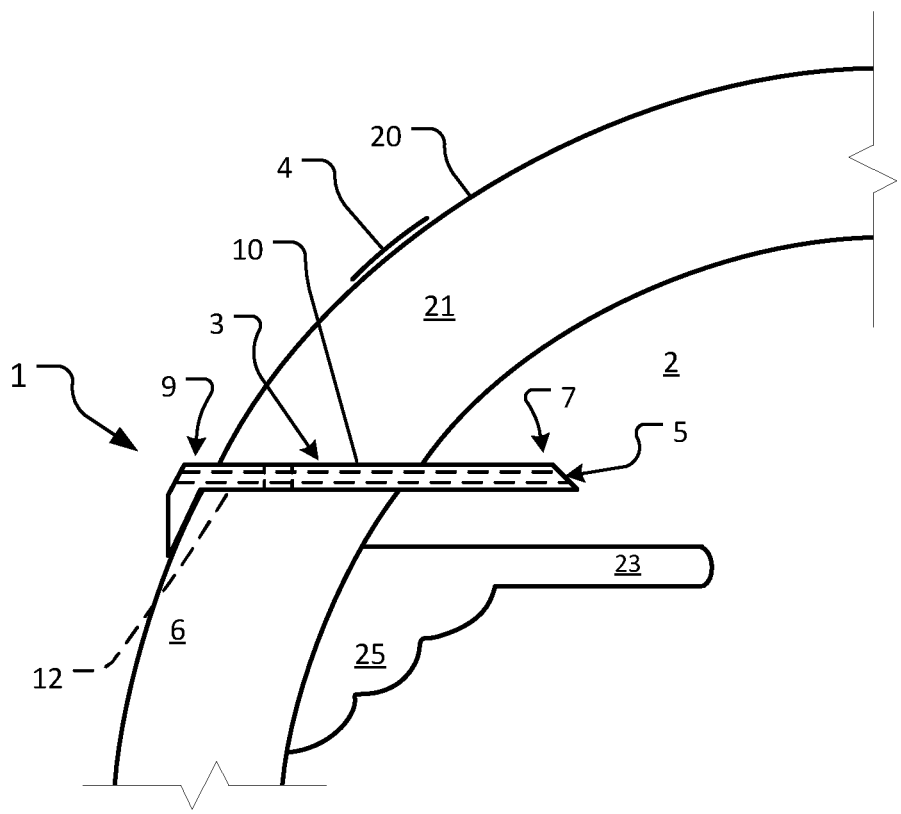
FIG. 1 is a sagittal cross-sectional schematic diagram of an eye with one embodiment of a device illustrative of the devices provided herein implanted in the eye.

Referring to FIG. 1, an example device 1 is shown implanted in an afflicted eye 20 for the purpose of treating dry eye in afflicted eye 20. The depicted anatomical features of eye 20 include an anterior chamber 2, a sclera 6, a tear film 4, an iris 23, a ciliary body 25, and a cornea 21. Device 1 includes a body 3 that defines a lumen 5. Body 3 includes a first end 7 and a second end 9. Body 3 has an external surface 10, and a lumenal surface 12.

As depicted, device 1 is configured to be surgically implanted in sclera 6 of eye 20. Device 1 has a length sufficient to provide fluid communication between anterior chamber 2 and tear film 4 of eye 20 when device 1 is implanted in sclera 6. As described further herein, in some embodiments, lumen 5 can be sized and configured to provide an appropriate outflow resistance to modulate aqueous humor flowing through lumen 5, without an element that provides additional flow resistance (e.g., a filter or a porous element). In doing so, lumen 5 functions to maintain a desired intraocular pressure (TOP), while also providing moisture and lubrication to the surface of eye 20 and tear film 4. In other words, aqueous humor is shunted directly to tear film 4. No conjunctival bleb is formed. Additionally, episcleral venous pressure (EVP) that could raise nocturnal IOP is avoided. In some cases, a device provided herein can define a lumen that includes a filter or a porous element.

In some cases, to provide fluid communication between anterior chamber 2 and tear film 4, device 1 has a length of about 2.5 mm. In some embodiments, device 1 has a length of between about 2.5 mm and about 5.0 mm, or between about 3.5 mm and about 6.0 mm. The length of at least about 2.5 mm will reduce the possibility of blockage of the lumenal opening in anterior chamber 2 by iris 23. The length of device 1 within the scleral tract would preferably be greater than the scleral thickness, because insertion would not be perpendicular to sclera 6 (but more tangential) to be parallel to iris 23.

In some embodiments, aqueous humor can be monitored in conjunction with device 1. For example, glucose levels can be monitored in the aqueous humor exiting through lumen 5 of body 3 of device 1. In some embodiments, techniques involving polarimetry and/or fluorescence can be used to monitor glucose levels in the aqueous humor exiting device 1. Monitoring glucose levels in the aqueous humor can correspond to glucose levels in blood. This can reduce or eliminate the need to draw blood for monitoring glucose levels in individuals benefiting from glucose monitoring, such as diabetic individuals. Device 1 can bring the aqueous humor to the surface of eye 20 to improve monitoring, such as through polarimetry. This can allow for more accurate glucose monitoring by monitoring aqueous humor instead of, for example, monitoring tears of eye 20. The tears of eye 20 can have a lower glucose levels as compared to aqueous humor.

Glucose levels in aqueous humor can correspond relatively directly to glucose levels in blood. In some cases, an individual's glucose levels in aqueous humor can be substantially the same as glucose levels in blood. Monitoring glucose levels in aqueous humor can, therefore, accurately predict glucose levels in the blood. In some cases, monitoring glucose levels in aqueous humor can be more accurate and reliable than monitoring glucose in tears, because tear glucose levels tend to be lower and less reliable than aqueous humor glucose levels. In some cases, monitoring glucose levels in aqueous humor can even be more accurate and reliable than monitoring glucose directly in the blood, because blood tends to have a large variety of non-glucose constituents that can complicate monitoring, whereas aqueous humor tends to have fewer non-glucose constituents.

Figure 2:
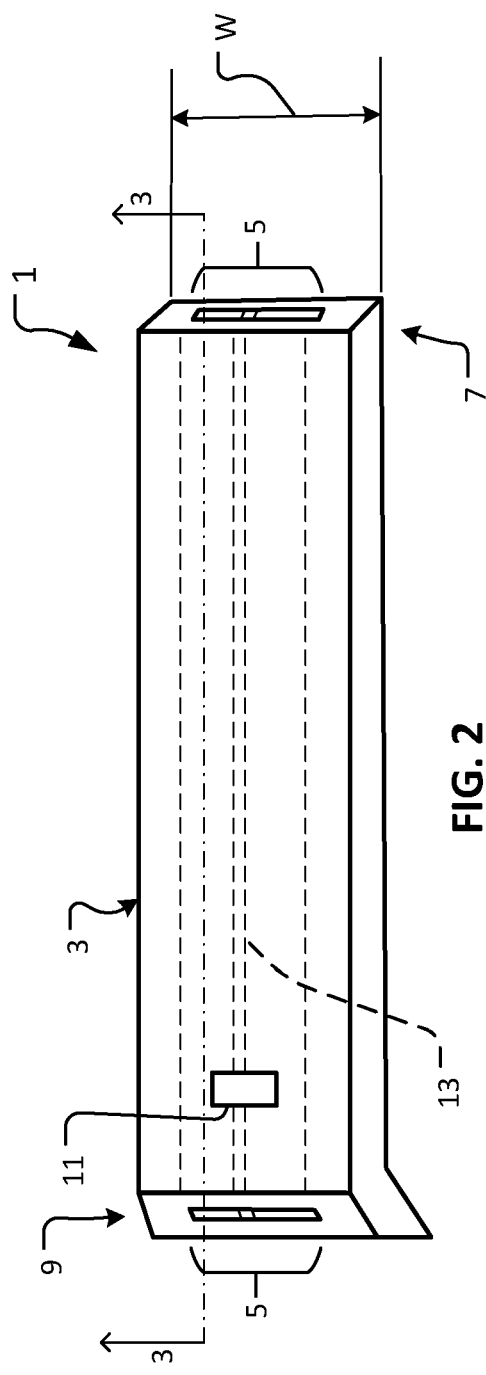
FIG. 2 is a perspective view of an example device for implantation in the eye in accordance with some embodiments.
Figure 3:
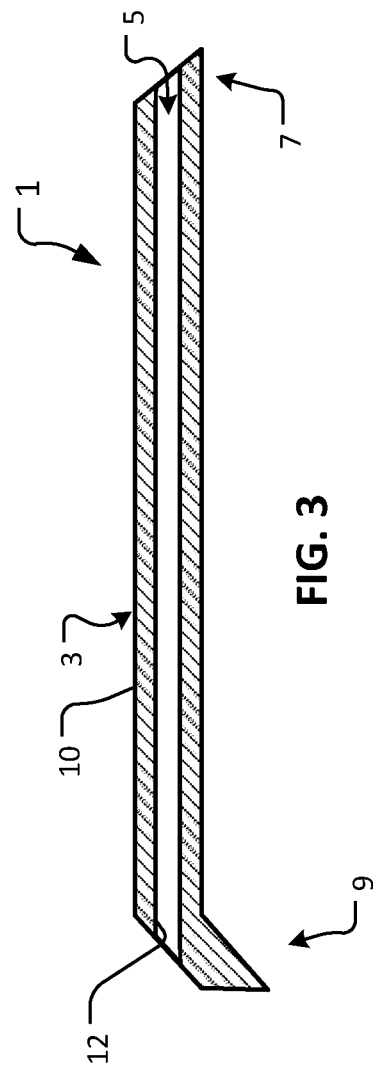
FIG. 3 is a longitudinal cross-sectional view of the device of FIG. 2.

Referring also to FIGS. 2 and 3, additional details and features of example device 1 are visible therein. FIG. 3 is a longitudinal cross-sectional view of device 1 along section line 3-3 as shown in FIG. 2. It should be understood that one or more (or all) of the details and features described herein in reference to example device 1 are also applicable to the other device embodiments provided herein.

In some embodiments, the main structure of body 3 is formed of a material such as, but not limited to, SU-8, parylene, thiolene, silicone, acrylic, polyimide, polypropylene, polymethyl methacrylate, polyethylene terephthalate (PET), polyethylene glycol (PEG), polyurethane, and expanded polytetrafluoroethylene (e.g., denucleated and coated with laminin). In some embodiments, the main structure of body 3 is formed of a combination of two or more materials. For example, in some embodiments, a layer of PEG is sandwiched between an upper layer of PET and a lower layer of PET. The PEG can be used to define lumen 5, in some embodiments. The use of PEG for the surfaces of the lumen can be advantageous because PEG resists bacterial, protein, and cell adherence.

In some embodiments, a portion of external surface 10 of body 3 is coated with a coating such as a silicone coating or other type of coating. In some embodiments, substantially the entire external surface 10 is coated with a coating such as a silicone coating or other type of coating. In particular embodiments, one portion of external surface 10 may be coated with silicone, and other one or more portions may be coated with another type or types of coatings. Embodiments that include a silicone coating on portions or all of external surface 10 may be coated with a layer of silicone about 50 µm thick, or within a range from about 40 µm to about 60 µm thick, or within a range from about 30 µm to about 70 µm thick, or within a range from about 20 µm to about 80 µm thick, or thicker than about 80 µm.

In some embodiments, external surface 10 of body 3 includes a porous cellular ingrowth coating on at least a portion thereof. In some embodiments, the portion of external surface 10 that is coated with the cellular ingrowth coating corresponds substantially to the portion of body 3 in contact with eye tissue (e.g., sclera 6) following scleral implantation. Such porous cellular ingrowth coatings have been described with respect to other ophthalmic implants, and can be made of silicone with a thickness of about 0.04 mm, in some examples. In some embodiments, surface laser engraving can be used to make depressions in a portion of the body surface to allow cellular ingrowth. Selected growth factors may be adsorbed on to this coating to enhance cellular ingrowth. Coating external surface 10 with a hetero-bifunctional crosslinker allows the grafting of naturally occurring extracellular matrix proteins such as collagen type 1, laminin, fibronectin, or other cell adhesion peptides (CAPs) to external surface 10. These can attract fibroblasts from the episclera to lead to collagen immobilization of device 1. One example of a hetero-bifunctional crosslinker that is useful for such a purpose is 5-azido-2-nitrobenzoic acid N-hydroxysuccinimide.

In some embodiments, one or more portions of body 3 may be configured to inhibit conjunctival overgrowth. For example, second end 9 (of which at least a portion thereof extends exterior to cornea 21) can be configured to inhibit conjunctival overgrowth. Preventing such conjunctival overgrowth can advantageously facilitate patency of lumen 5. In some such embodiments, a coating such as a PEG coating can be applied to second end 9 to inhibit conjunctival overgrowth.

In some embodiments, a bio-inert polymer is included as a liner of lumen 5. That is, in some embodiments, lumenal surface 12 includes a bio-inert polymer material. For example, in some embodiments, a material such as, but not limited to, polyethylene glycol (PEG), phosphoryl choline (PC), or polyethylene oxide (PEO) can be used for the lumenal surface 12 of lumen 5. Such bio-inert surfaces may be further modified with biologically active molecules such as heparin, spermine, surfactants, proteases, or other enzymes, or other biocompatible chemicals amendable to surface immobilization or embedding. Some such materials are advantageously hydrophilic. For example, in some embodiments, the hydrophilic properties of lumenal surface 12 can help prevent bacterial contamination of device 1.

In some embodiments, a filter or filter-like porous member is included in the device's flow path (e.g., lumen 5) for the aqueous humor. In some embodiments, no filter or porous member is present in lumen 5 for the purpose of resisting ingress of bacteria. In some cases, the surface chemistry of lumen 5 of a device provided herein can be used to prevent bacterial ingress. For example, the high molecular weight PEG lining lumen 5 can be very hydrophilic and can attract a hydration shell. The motility of the PEG side chains, and steric stabilization involving these side chains, also can repulse bacteria, cells, and proteins. In some cases, the shear stress of the laminar flow of the aqueous humor as it leaves eye 20 can resist ingress of bacteria into device 1. Experiments demonstrated that when perfusing device 1 into an external broth with $10^8$ bacteria per mL, no bacteria entered device 1. Tears are usually quite sterile and have IgA, lysozyme, lactoferrin, and IgG/complement if inflamed. In some cases, tears can be used to clear an infection.

In some embodiments, device 1 is constructed using bulk and surface micro-machining. In some embodiments, device 1 is constructed using 3D micro-printing. In particular embodiments, external surface 10 is textured such as by stippling, cross-hatching, waffling, roughening, placing backwards facing barbs or protrusions, and the like. One way to accomplish this external surface texturing is by laser engraving. Such featuring can stabilize device 1 in situ and also can increase the visibility of device 1 by making it less transparent. The featuring of the external surface 10 can make device 1 more visible to a surgeon, thereby making the handling and deployment process of device 1 more efficient and convenient.

In some embodiments, the width W of device 1 is in a range from about 0.7 mm to about 1.0 mm, or from about 0.9 mm to about 1.2 mm, or from about 1.1 mm to about 1.4 mm, or from about 1.3 mm to about 1.6 mm, or from about 1.5 mm to about 1.8 mm, or greater than about 1.8 mm.

In the depicted embodiment, body 3 flares and/or extends out around at least part of second end 9. The flaring of body 3 at its second end 9 provides a number of advantages. For example, flaring of body 3 at its second end 9 aids in the surface mounting of device 1 in eye 20 by providing an endpoint of insertion as device 1 is pushed into sclera 6 during surgery. Additionally, the flaring of body 3 at its second end 9 provides structural support to bolster the portion of device 1 that protrudes from eye 20. Such structural support can help maintain patency of lumen 5 by resisting deflection of the protruding portion, which may tend to occur from the forces exerted by an eyelid, for example. For instance, such a posteriorly placed flare/extension bolsters the device against posterior pressures. In some cases, the flaring/extending of body 3 at its second end 9 provides additional resistance to growth of conjunctiva over the exposed second end 9. For example, the additional surface area provided by the flared portion may tend to make growth of conjunctiva over the exposed second end 9 less likely to occur, thereby helping to maintain patency of lumen 5.

In some cases, device 1 can be anteriorly beveled at its first end 7 to assist in implantation and to keep the iris from plugging the inner lumenal opening.

In the depicted embodiment, lumen 5 is a narrow slit with a generally rectangular cross-section. This narrow slit may contain a number of longitudinal channels, which themselves may be square, rectangular, circular, or the like, and combinations thereof. In some embodiments, the total width of lumen 5 is about 0.5 mm. In some embodiments, the total width of lumen 5 is in a range from about 0.4 mm to about 0.6 mm, or about 0.3 mm to about 0.7 mm, or about 0.2 mm to about 0.8 mm. The height, effective width, configuration, and length of lumen 5 can be selected to provide a total resistance so that an TOP from about 8 mm Hg to about 12 mm Hg is maintained, while concurrently shunting an amount of aqueous humor to the tear film of the eye to treat dry eye conditions and/or glaucoma.

The effective width of lumen 5 is that width obtained after subtracting the total width of all the device support ribs 13 (as shown in FIG. 2). In some implementations, it is desirable to design lumen 5 to have an aqueous humor outflow resistance such that the TOP remains in a normal range of about 8 mm Hg to about 12 mm Hg. Doing so will help ensure that normal aqueous humor outflow process (the conventional or trabecular meshwork pathway) of the eye remains operative, while concurrently shunting an amount of aqueous humor to the tear film of the eye to treat dry eye conditions or glaucoma. Poiseuille's equation for laminar flow though a porous media (R=8×viscosity×channel length/channel number×π×channel radius to the fourth power) can be used to determine the combination of lumen dimensions to attain the proper resistance to provide the desired TOP while concurrently shunting an amount of aqueous humor to the tear film of the eye to treat dry eye conditions or glaucoma.

In the depicted embodiment, device 1 includes a suture attachment feature 11. In the depicted embodiment, suture attachment feature 11 is a through-hole that extends completely through body 3. Suture attachment feature 11 can receive a suture therethrough, whereby body 3 is attached to eye 20. In some implementations, such suture(s) can stabilize device 1 in eye 20 prior to bio-integration of device 1 with eye 20. In some embodiments, one or more other types of suture attachment features are included such as a flange, a slot, a projection, a clamp, and the like. In the depicted embodiment, suture attachment feature 11 is a rectangular hole. In some embodiments, suture attachment feature 11 is a circular hole, ovular hole, or another shape of hole.

In some embodiments, suture attachment feature 11 is sized large enough to receive a 10-0 spatula needle. For example, in some embodiments, the dimensions of suture attachment feature 11 is about 300 μm by about 200 μm. Other appropriate sizes for suture attachment feature 11 can be used.

In some embodiments, one or more longitudinal support ribs 13 is included within lumen 5. Support rib 13 can add structural rigidity to help maintain patency of lumen 5. In some embodiments, support rib 13 includes a series of short discontinuous ribs that are disposed along lumen 5. In some embodiments, no support rib 13 is included.

In some embodiments, longitudinal support ribs 13 can divide lumen 5 into two or more portions (e.g., channels). That is, in some embodiments, lumen 5 of body 3 includes two or more channels (e.g., two, three, four, five, six, or more than six channels). Aqueous outflow can occur through these channels, which may be square, rectangular, circular, and the like, and combinations thereof.

In some embodiments, the portion of body 3 that is in contact with eye tissue following implantation includes one or more barbs designed to engage with tissue upon implantation and provide stability to implanted device 1. The one or more barbs may be formed as part of device body 3 during manufacture, or may be fused or bonded to device body 3 using any appropriate technique.

It should be understood that one or more (or all) of the details and features described herein in reference to example device 1 are also applicable to the other device embodiments provided herein. Moreover, one or more of the device details and features described herein can be combined with one or more other device details and features described herein to create hybrid device constructions, and such hybrid device constructions are within the scope of this disclosure.

Figure 4:
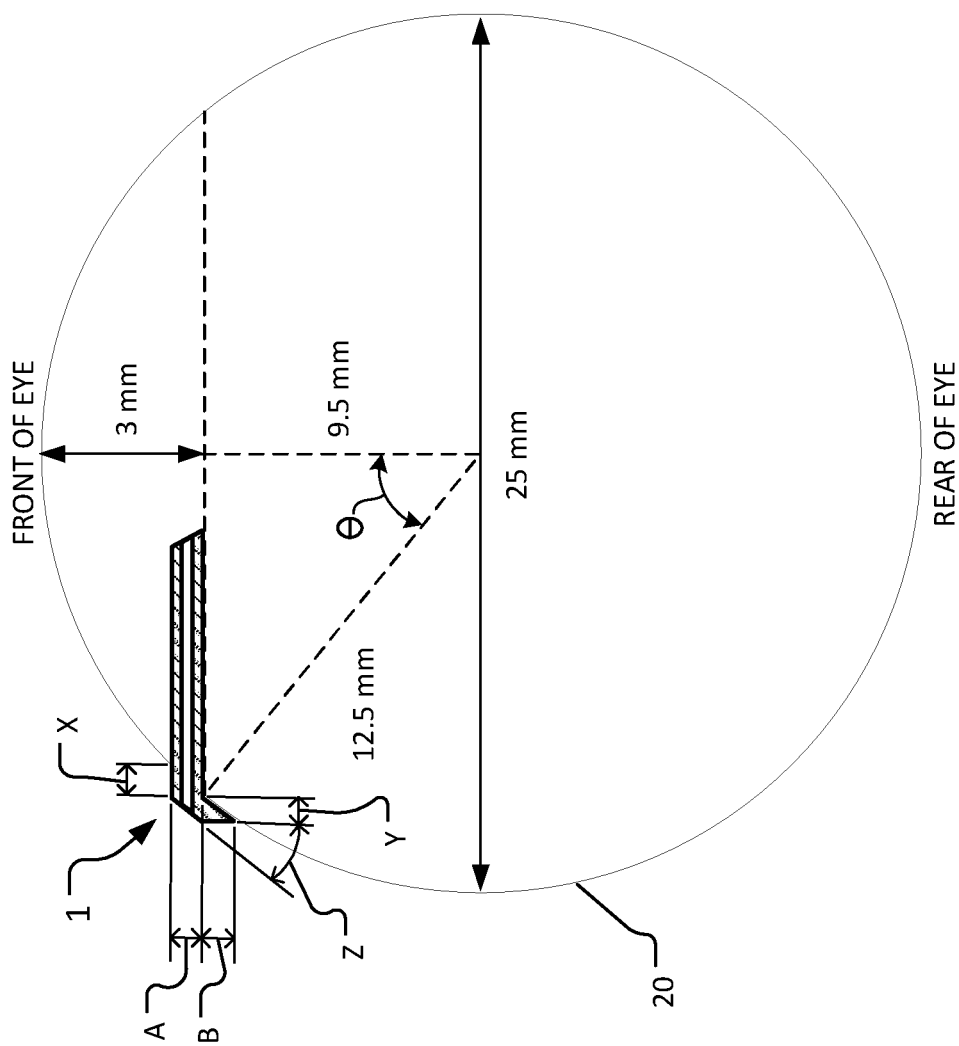
FIG. 4 is a schematic drawing of a sagittal cross-section of an eye (dividing the nasal and temporal halves of the eye) that shows example geometric relationships between the eye and an implanted device for treating dry eye.

Referring also to FIG. 4, certain geometric aspects of device 1 in relation to eye 20 can be described. Device 1 is shown implanted at the limbus of eye 20. The dimension X is the anterior protrusion of device 1 from the scleral surface, and the dimension Y is the posterior protrusion of device 1 from the scleral surface. In the depicted implementation, dimensions X and Y are about the same because flare bevel angle Z follows the contour of eye 20 (e.g., angle θ is about 40° to 45° in the depicted implementation). The posterior flare and/or extension also follows the contour of eye 20. Protrusion of device 1 from the scleral surface can prevent conjunctival overgrowth. In some cases, this advantage should be balanced with the fact that increased protrusion may tend to make for increased micromotion in some cases. In some embodiments, protrusion dimensions X and Y are in a range from about 50 μm to about 1000 μm, or from about 50 μm to about 200 μm, or from about 100 μm to about 300 μm, or from about 200 μm to about 400 μm, or from about 300 μm to about 500 μm, or from about 400 μm to about 600 μm, or from about 500 μm to about 700 μm, or from about 600 μm to about 800 μm, or from about 700 μm to about 900 μm, or from about 800 μm to about 1,000 μm.

Dimension A in FIG. 4 is the thickness of device 1. Dimension B is the frontal view thickness of the flared portion of device 1. In some embodiments, facial dimensions A and B are about 200 μm. Dimension B can vary in correspondence to variations in selected protrusion dimensions X and Y.

Figure 5:
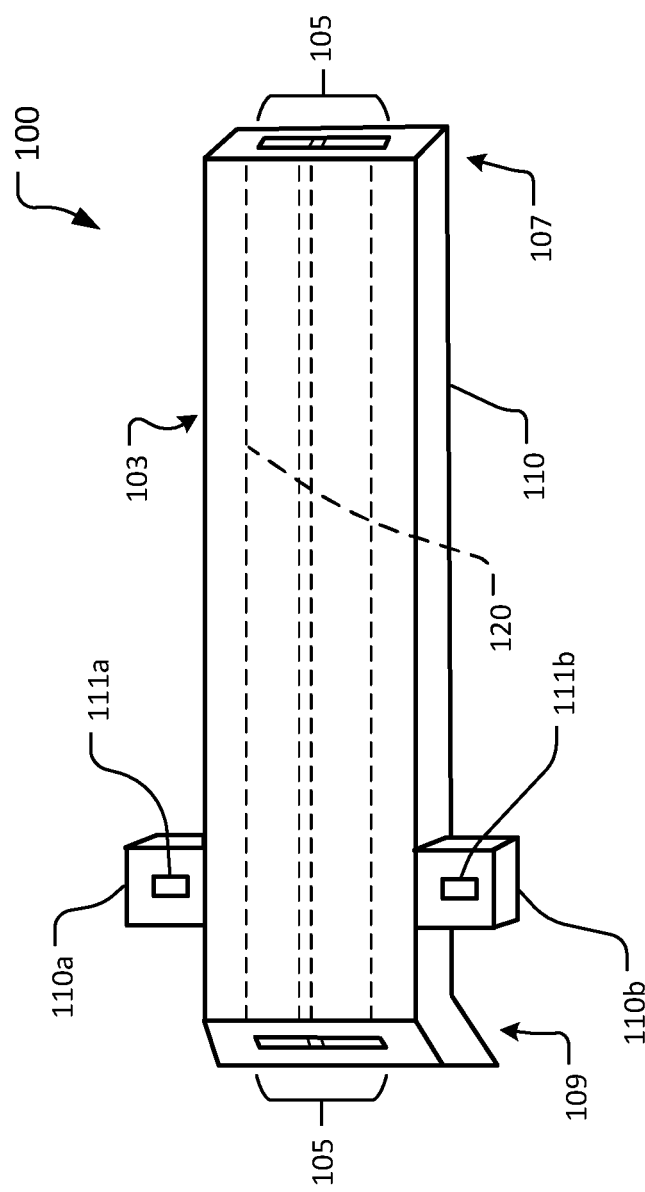
FIG. 5 is a perspective view of another example device in accordance with some embodiments.

Referring to FIG. 5, another example device 100 in accordance with some embodiments provided herein is illustrated. Device 100 includes a body 103 that defines a lumen 105. Body 103 includes a first end 107 and a second end 109. Body 103 has an external surface 110 and a lumenal surface 120.

Device 100 can be constructed using any of the materials and techniques as described above in reference to device 1. In some cases, device 100 can be configured and used as described above in reference to device 1. Device 100 differs from device 1, at least in regard to, the addition of lateral wings 110a and 110b. Further, in the depicted embodiment of device 100, device 100 does not include suture attachment feature 11 as included in device 1. Rather, device 100 includes suture attachment features 111a and 111b that are disposed in wings 110a and 110b, respectively. Each of suture attachment features 111a and 111b can be configured like suture attachment feature 11 of device 1 as described above.

A first method for installing the devices provided herein is as follows. Sometime before installation, the eye is irrigated with 1-5% Betadine solution, and topical antibiotic and non-steroidal anti-inflammatory drops (NSAID) are applied to the operative eye. These can be continued for about one week postoperatively four times a day. The NSAID helps stabilize the blood-aqueous barrier.

Each of the embodiments of the device illustrated herein may be inserted under topical anesthesia, possibly supplemented subconjunctivally. In general, the devices provided herein may be inserted into the sclera and through the conjunctiva, using an operative procedure. The location of insertion of a device provided herein can be in the sclera at about the posterior surgical limbus. In some cases, a device provided herein can be inserted at any site around the limbus. In some cases, a device provided herein can be inserted at the superior or temporal limbus.

In some cases, the insertion procedure can begin by excising a small amount of conjunctiva at the site of the anticipated insertion, exposing the underlying sclera. In some cases (as described further below), the insertion procedure is performed without the excision of conjunctiva. Any bleeding can then be cauterized. For embodiments of the device as shown in FIG. 5, a groove incision can be made at the site of insertion with a diamond blade with a depth guard to a depth sufficient to cover the entire length of wings 110a and 110b when the device is in place. Wings 110a and 110b can provide an end-stop for insertion, so the flare at end 109 of device 100 is optional. This groove incision can be made at or near the posterior surgical limbus and can be parallel to the iris plane. For the embodiment of device 1 of FIG. 2, no groove incision is needed, since this is only necessitated by wings 110a and 110b. In some cases, for device 1, only a straight stab incision is used, with the end-stop for insertion depth provided by the flare/extension at the outer end of the device. In some cases, for device 1, insertion can be made through intact conjunctiva.

Approximately 1-2 mm posterior to the limbus, at the site of the now exposed sclera, a diamond blade can be used to make a stab incision into the anterior chamber, while held roughly parallel to the iris. This blade is of a size predetermined to make an opening into the anterior chamber sized appropriately for the introduction of the device. This stab incision is made gently, but relatively quickly, assiduously avoiding any and all intraocular structures. Such an uneventful paracentesis has been found not to disrupt the blood-aqueous barrier in most cases. In any event, any disruption of this barrier is usually of less than 24 hours duration without continued insult.

The device is next picked up and held with a non-toothed forceps. The lips of the stab incision wound may be gaped with a fine, toothed forceps. The pointed tip of the tube element would then be gently pushed through the scleral tract of the stab incision and into the anterior chamber, with the device lying above and parallel to the iris, with the bevel up (i.e., anteriorly). The flare/extension in the embodiments of device 1 and device 100 provide for a definite endpoint to the depth of insertion. For embodiments of the device having a beveled first end, the bevel is oriented anteriorly to minimize the potential for blockage of the lumenal opening by the iris. The scleral barb(s) or other outer surface features (if included) stabilize the device until the biointegration with the sclera is complete. This biointegration is a function of its porous cellular ingrowth surface, possibly enhanced by adsorbed growth factors and/or grafted extracellular matrix proteins. In addition, in some implementations, one or more sutures may be added using the device's suture attachment features to stabilize the device prior to biointegration. For example, in the embodiments of device 1 and device 100, a 10-0 nylon suture on a broad spatula needle may be used to suture the device the sclera, providing additional stability to the device until the biointegration is complete. This suture may then be easily removed at a later time if needed. An alternative insertion technique would have the device preloaded into an insertion holder or cartridge, to limit the needed handling of the device by the surgeon. A properly sized sharp blade could be at the leading edge of the inserter, such blade acting also as a guide for implanting the device. Alternatively, the paracentesis could be made with a separate blade, followed by controlled insertion with an inserter.

After insertion of the device, an ocular shield can be placed over the eye. The implanted device will bio-integrate with the sclera, thereby reducing the risks of infections such as tunnel infection.

Referring to FIGS. 6 and 7, another example device 600 in accordance with some embodiments provided herein is illustrated. Device 600 includes a body 603 that defines a lumen 605. Body 603 includes a first end 607 and a second end 609. Body 603 has an external surface 610 and a lumenal surface 612.

Device 600 can be constructed using any of the materials and techniques as described herein in reference to device 1. Also, device 600 can be configured and used in any of the manners described herein in reference to device 1.

In the depicted embodiment, first end 607 is generally orthogonal in relation to the longitudinal surfaces of external surface 610. In contrast, second end 609 of the depicted embodiment is beveled in relation to the longitudinal surfaces of external surface 610. It should be understood that, in some embodiments of device 600 and the other devices provided herein, both ends 607 and 609 may be beveled (e.g., like second end 609), both ends 607 and 609 may be orthogonal (e.g., like first end 607), or either one of ends 607 or 609 may be beveled while the other one of ends 607 or 609 is orthogonal.

In the depicted embodiment, lumen 605 includes a first longitudinal rib 613a and a second longitudinal rib 613b. While in the depicted embodiment, the ribs 613a and 613b extend continuously from first end 607 to second end 609, in some embodiments, ribs 613a and 613b may be made of multiple individually shorter segments, rib portions, and/or other arrangements. That is, it should be understood that lumen 605 may be configured with any of the lumenal constructs provided herein (e.g., FIGS. 15-26, and others), and combinations thereof.

In the depicted embodiment, second end 609 includes a first flange portion 614a and a second flange portion 614b that extend laterally in relation to the longitudinal axis of body 603. In some implementations, surfaces of flange portions 614a and 614b contact the surface of the cornea and provide mechanical stabilization of device 600 in relation to the eye. The outermost lateral surfaces of flange portions 614a and 614b are radiused (contoured) in the depicted embodiment. In some embodiments, the outermost lateral surfaces of flange portions 614a and 614b are planar and parallel to the longitudinal surfaces of external surface 610. In some embodiments, the outer lateral surfaces of flange portions 614a and 614b are planar and unparallel or askew in relation to the longitudinal surfaces of external surface 610.

In some embodiments, one or more suture attachment features are included on device 600 (and the other devices provided herein). In the depicted embodiment, second end 609 includes a first suture attachment structure 616a and a second suture attachment structure 616b. The suture attachment structures 616a and 616b are slots in the depicted embodiment. In some embodiments, other types of suture attachment structures can be alternatively or additionally included. While the depicted embodiment includes two suture attachment structures 616a and 616b, in some embodiments, zero, one, three, four, or more than four suture attachment structures are included.

One or more portions of external surface 610 can be configured for enhanced friction with eye tissue (e.g., the cornea or sclera). Advantageous mechanical stability and/or migration resistance of the device 600 (and the other devices provided herein) in relation to the eye can be facilitated by such portions. For example, in the depicted embodiment, a surface portion 618 includes an enhanced texture (roughness) in comparison to other portions of external surface 610. In the depicted embodiment, surface portion 618 is a waffled surface (cross-hatched). In some embodiments, other types of texturing configurations can be alternatively or additionally included. For example, such texturing configurations can include, but are not limited to, stippling, knurling, inclusion of one or more barbs, and the like, and combinations thereof. In some embodiments, the surface portion 618 is created by techniques such as, but not limited to, laser machining, chemical etching, 3D printing, photo etching, and the like.

Figure 8:
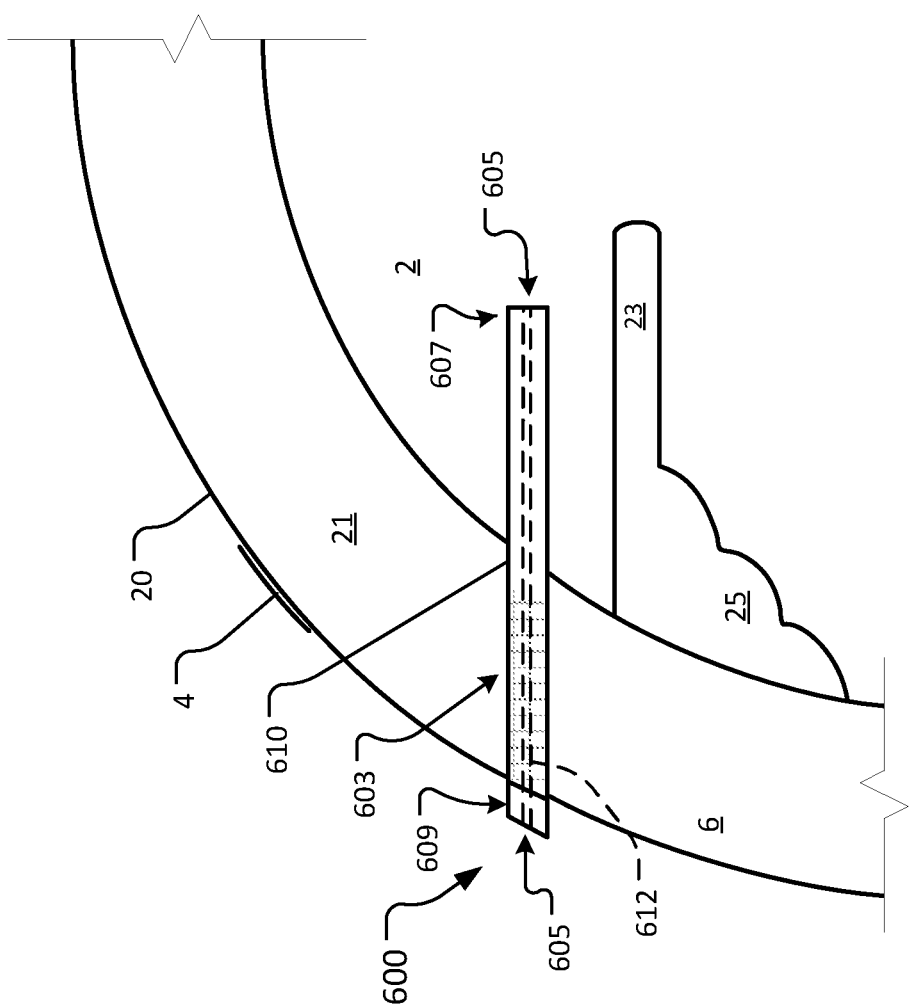
FIG. 8 is a sagittal cross-sectional schematic diagram of an eye with the device of FIG. 6 implanted in the eye.

Referring to FIG. 8, device 600 is shown implanted in afflicted eye 20 for the purpose of treating glaucoma of or a dry eye condition in afflicted eye 20. The depicted anatomical features of eye 20 include anterior chamber 2, sclera 6, tear film 4, iris 23, ciliary body 25, and cornea 21. Device 600 includes body 603 that defines lumen 605. Body 603 includes first end 607 and a second end 609. Body 603 has an external surface 610, and a lumenal surface 612.

As depicted, device 600 (and the other devices provided herein) is configured to be surgically implanted in sclera 6 of eye 20. Device 600 has a length sufficient to provide fluid communication between anterior chamber 2 and tear film 4 of eye 20 when device 600 is implanted in sclera 6. As described further below, in some embodiments lumen 605 is sized and configured to provide an appropriate outflow resistance to modulate aqueous humor flowing through lumen 605, without the need for an element that provides additional flow resistance (e.g., a filter or a porous element). In doing so, lumen 605 functions to maintain a desired IOP, while also providing moisture and lubrication to the surface of eye 20 and tear film 4. In some embodiments, a filter or filter-like porous element is includes in lumen 605.

In general, to provide fluid communication between anterior chamber 2 and tear film 4, in some embodiments, device 600 has a length of about 2.5 mm. In some embodiments, device 600 has a length of from about 2.5 mm to about 5.0 mm, or from about 3.5 mm to about 6.0 mm. The length of at least about 2.5 mm will reduce the possibility of blockage of the lumenal opening in anterior chamber 2 by iris 23. The length of device 600 within the scleral tract would preferably be greater than the scleral thickness, because insertion would not be perpendicular to sclera 6 (but more tangential) to be parallel to iris 23.

Referring to FIGS. 9 and 10, another example device 700 in accordance with some embodiments provided herein is illustrated. Device 700 includes a body 703 that defines a lumen 705. Body 703 includes a first end 707 and a second end 709. Body 703 has an external surface 710 and a lumenal surface 712.

Device 700 can be constructed using any of the materials and techniques as described herein in reference to device 1. Also, device 700 can be configured and used in any of the manners described herein in reference to device 1.

In the depicted embodiment, first end 707 is beveled in relation to the longitudinal surfaces of external surface 710. Second end 709 of the depicted embodiment is also beveled in relation to the longitudinal surfaces of external surface 710. It should be understood that, in some embodiments of device 700 (and the other devices provided herein), both ends 707 and 709 may be beveled (e.g., as shown), both ends 707 and 709 may be orthogonal, or either one of ends 707 or 709 may be beveled while the other one of ends 707 or 709 is orthogonal.

In the depicted embodiment, lumen 705 includes a plurality of ovular pillars 713 that are spaced apart from each other. It should be understood that lumen 705 may be configured with any of the lumenal constructs provided herein (e.g., FIGS. 15-26, and others), and combinations thereof.

In the depicted embodiment, second end 709 includes a first flange portion 714a and a second flange portion 714b. In some implementations, flange portions 714a and 714b contact the surface of the cornea and provide mechanical stabilization of device 700 in relation to the eye. The outer lateral surfaces of flange portions 714a and 714b include planar and chamfered portions in the depicted embodiment. In some embodiments, the outer lateral surfaces of flange portions 714a and 714b are radiused (contoured) in relation to the longitudinal surfaces of external surface 710.

In some embodiments, one or more suture attachment features are included on device 700 (and the other devices provided herein). In the depicted embodiment, second end 709 includes a suture attachment structure 716. The suture attachment structure 716 is a slot in the depicted embodiment. In some embodiments, other types of suture attachment structures can be alternatively or additionally included. While the depicted embodiment includes one suture attachment structure 716, in some embodiments, zero, two, three, four, or more than four suture attachment structures are included.

One or more portions of external surface 710 can be configured for enhanced friction with eye tissue (e.g., the cornea or sclera). Such portions can provide advantageous mechanical stability and/or migration resistance of the device 700 (and the other devices provided herein) in relation to the eye. For example, in the depicted embodiment, a surface portion 718 includes an enhanced texture (roughness) in comparison to other portions of external surface 710. In the depicted embodiment, surface portion 718 is a stippled surface. In some embodiments, other types of texturing configurations can be alternatively or additionally included. For example, such texturing configurations can include, but are not limited to, cross-hatching, knurling, inclusion of one or more barbs, and the like, and combinations thereof. In some embodiments, the surface portion 718 is created by techniques such as, but not limited to, laser machining, chemical etching, 3D printing, photo etching, and the like.

Referring to FIGS. 11 and 12, another example device 800 in accordance with some embodiments provided herein is illustrated. Device 800 includes a body 803 that defines a lumen 805. Body 803 includes a first end 807 and a second end 809. Body 803 has an external surface 810 and a lumenal surface 812.

Device 800 can be constructed using any of the materials and techniques as described herein in reference to device 1. Also, device 800 can be configured and used in any of the manners described herein in reference to device 1.

In the depicted embodiment, first end 807 is beveled. Second end 809 of the depicted embodiment is also beveled in relation to the longitudinal surfaces of external surface 810. It should be understood that, in some embodiments of device 800 and the other devices provided herein, both ends 807 and 809 may be orthogonal in relation to the longitudinal surfaces of external surface 810, or either one of ends 807 or 809 may be beveled while the other one of ends 807 or 809 is orthogonal.

In the depicted embodiment, lumen 805 includes a longitudinal rib 813. While in the depicted embodiment, the rib 813 extends continuously from first end 807 to second end 809, in some embodiments, rib 813 may be made of multiple individually shorter segments and/or other arrangements. It should be understood that lumen 805 may be configured with any of the lumenal constructs provided herein (e.g., FIGS. 15-26, and others), and combinations thereof.

In the depicted embodiment, second end 809 includes a first flange portion 814a and a second flange portion 814b. In some implementations, one or more surfaces of flange portions 814a and 814b contact the surface of the cornea and provide mechanical stabilization of device 800 in relation to the eye. The outer lateral surfaces of flange portions 814a and 814b are planar and parallel to the longitudinal surfaces of external surface 810 in the depicted embodiment. In some embodiments, the outer lateral surfaces of flange portions 814a and 814b are contoured. In some embodiments, the outer lateral surfaces of flange portions 814a and 814b are planar and unparallel or askew in relation to the longitudinal surfaces of external surface 810.

In some embodiments, one or more suture attachment features are included on device 800 (and the other devices provided herein). In the depicted embodiment, second end 809 includes a first suture attachment structure 816a and a second suture attachment structure 816b. The suture attachment structures 816a and 816b are holes in the depicted embodiment. In some embodiments, other types of suture attachment structures can be alternatively or additionally included. While the depicted embodiment includes two suture attachment structures 816a and 816b, in some embodiments, zero, one, three, four, or more than four suture attachment structures are included.

One or more portions of external surface 810 can be configured for enhanced friction with eye tissue (e.g., the cornea or sclera). Advantageous mechanical stability and/or migration resistance of the device 800 (and the other devices provided herein) in relation to the eye can be facilitated by such portions. For example, in the depicted embodiment, a plurality of protrusions 818 provide an enhanced texture (greater roughness) in comparison to other portions of external surface 810. In the depicted embodiment, protrusions 818 are disposed on opposing surfaces of external surface 810. It should be understood that protrusions 818 can be located in any desired location(s) on external surface 810. In some embodiments, other types of texturing configurations can be alternatively or additionally included. For example, such texturing configurations can include, but are not limited to, cross-hatching, stippling, knurling, inclusion of one or more barbs, and the like, and combinations thereof. In some embodiments, the surface portion 818 is created by techniques such as, but not limited to, laser machining, chemical etching, 3D printing, photo etching, and the like.

Referring to FIGS. 13 and 14, another example device 900 in accordance with some embodiments provided herein is illustrated. Device 900 includes a body 903 that defines a lumen 905. Body 903 includes a first end 907 and a second end 909. Body 903 has an external surface 910 and a lumenal surface 912.

Device 900 can be constructed using any of the materials and techniques as described herein in reference to device 1. Also, device 900 can be configured and used in any of the manners described herein in reference to device 1.

In the depicted embodiment, first end 907 is not beveled. Rather, first end 907 is generally orthogonal in relation to the longitudinal surfaces of external surface 910. Second end 909 of the depicted embodiment is beveled in relation to the longitudinal surfaces of external surface 910. It should be understood that, in some embodiments of device 900 (and the other devices provided herein), both ends 907 and 909 may be beveled (e.g., like second end 909), both ends 907 and 909 may be orthogonal (e.g., like first end 907), or either one of ends 907 or 909 may be beveled while the other one of ends 907 or 909 is orthogonal.

In the depicted embodiment, lumen 905 includes a first longitudinal rib 913a and a second longitudinal rib 913b. While in the depicted embodiment, the ribs 913a and 913b extend continuously from first end 907 to second end 909, in some embodiments, ribs 913a and 913b may be made of multiple individually shorter segments and/or other arrangements. It should be understood that lumen 905 may be configured with any of the lumenal constructs provided herein (e.g., FIGS. 15-26, and others), and combinations thereof.

In the depicted embodiment, second end 909 includes a first flange portion 914a and a second flange portion 914b. In some implementations, flange portions 914a and 914b contact the surface of the cornea and provide mechanical stabilization of device 900 in relation to the eye. The outer lateral surfaces of flange portions 914a and 914b are planar and parallel to the longitudinal surfaces of external surface 910 in the depicted embodiment. In some embodiments, the outer lateral surfaces of flange portions 914a and 914b are nonplanar (e.g., radiused, chamfered, contoured, etc.). In some embodiments, the outer lateral surfaces of flange portions 914a and 914b are planar and unparallel or askew in relation to the longitudinal surfaces of external surface 910.

In some embodiments, one or more suture attachment features are included on device 900 (and the other devices provided herein). In the depicted embodiment, second end 909 includes a first suture attachment structure 916a and a second suture attachment structure 916b. The suture attachment structures 916a and 916b are slots in the depicted embodiment. In some embodiments, other types of suture attachment structures can be alternatively or additionally included. While the depicted embodiment includes two suture attachment structures 916a and 916b, in some embodiments, zero, one, three, four, or more than four suture attachment structures are included.

One or more portions of external surface 910 can be configured for enhanced friction with eye tissue (e.g., the cornea or sclera). Advantageous mechanical stability and/or migration resistance of the device 900 (and the other devices provided herein) in relation to the eye can be facilitated by such portions. For example, in the depicted embodiment, one or more lateral barbs 918 are included on opposing surfaces of external surface 910. In the depicted embodiment, lateral barbs 918 are triangular protrusions with atraumatic tips (e.g., truncated tips, radiused tips, and the like). In some embodiments, no such lateral barbs 918 are included. In some embodiments, other types of texturing configurations can be alternatively or additionally included. For example, such texturing configurations can include, but are not limited to, stippling, knurling, cross-hatching, and the like, and combinations thereof. In some embodiments, the surface portion 918 is created by techniques such as, but not limited to, laser machining, chemical etching, 3D printing, photo etching, and the like.

FIGS. 15-26 depict various example lumenal structures that can be incorporated in the devices provided herein. It should be understood that the lumenal structures depicted are not an exhaustive compilation of structures that can be used for configuring the lumenal passageways of the devices provided herein. Moreover, the features of one or more of the depicted lumenal structures can be combined with the features of one or more other depicted lumenal structures to create many different combinations, which are within the scope of this disclosure.

The example lumenal structures can be sized and configured to provide an appropriate outflow resistance to modulate aqueous humor flowing through the lumen without the need for an element that provides additional flow resistance (e.g., a filter or a porous element). In doing so, the lumen functions to maintain a desired IOP, while also providing moisture and lubrication to the surface of eye and tear film. In some embodiments, a filter or filter-like porous element is included in the devices provided herein.

Referring to FIG. 15, an example device 1000 can include a lumenal structure 1005 that includes one or more longitudinal ribs 1013. In the depicted embodiment, eight longitudinal ribs 1013 are included. In some embodiments, zero, one, two, three, four, five, six, seven, nine, ten, eleven, twelve, or more than twelve longitudinal ribs 1013 are included. Such longitudinal ribs 1013 serve to divide overall lumen 1005 into two or more longitudinal portions.

Referring to FIG. 16, an example device 1100 can include a lumenal structure 1105 that includes one or more longitudinal rib portions 1113. Such longitudinal rib portions 1113 serve to divide overall lumen 1105 into some segments having two or more longitudinal portions, and some segments that are undivided by longitudinal rib portions 1113. In the depicted embodiment, eight longitudinal rib portions 1113 are included. In some embodiments, zero, one, two, three, four, five, six, seven, nine, ten, eleven, twelve, or more than twelve longitudinal rib portions 1113 are included. Any suitable number of groupings of longitudinal rib portions 1113 can be included.

Referring to FIG. 17, an example device 1200 can include a lumenal structure 1205 that includes one or more longitudinal rib portions 1213. Such longitudinal rib portions 1213 serve to divide overall lumen 1205 into some segments having two or more longitudinal portions, and some segments that are undivided by longitudinal rib portions 1213. In addition, in the depicted embodiment, alternating groupings of longitudinal rib portions 1213 are laterally offset from adjacent groupings of longitudinal rib portions 1213. In the depicted embodiment, eight longitudinal rib portions 1213 are included. In some embodiments, zero, one, two, three, four, five, six, seven, nine, ten, eleven, twelve, or more than twelve longitudinal rib portions 1213 are included. Any suitable number of groupings of longitudinal rib portions 1213 can be included.

Referring to FIG. 18, an example device 1300 can include a lumenal structure 1305 that includes one or more longitudinal ribs 1313. In the depicted embodiment, six longitudinal ribs 1313 are included. In some embodiments, zero, one, two, three, four, five, seven, eight, nine, ten, eleven, twelve, or more than twelve longitudinal ribs 1313 are included. Such longitudinal ribs 1313 serve to divide overall lumen 1305 into two or more longitudinal portions. Longitudinal ribs 1313 can be made to have any suitable width.

Referring to FIG. 19, an example device 1400 can include a lumenal structure 1405 that includes one or more longitudinal rib portions 1413. Such longitudinal rib portions 1413 serve to divide overall lumen 1405 into some segments having two or more longitudinal portions, and some segments that are undivided by longitudinal rib portions 1413. In the depicted embodiment, six longitudinal rib portions 1413 are included. In some embodiments, zero, one, two, three, four, five, seven, eight, nine, ten, eleven, twelve, or more than twelve longitudinal rib portions 1413 are included. Any suitable number of groupings of longitudinal rib portions 1413 can be included. Longitudinal ribs 1313 can be made to have any suitable width.

Referring to FIG. 20, an example device 1500 can include a lumenal structure 1505 that includes one or more longitudinal rib portions 1513. Such longitudinal rib portions 1513 serve to divide overall lumen 1505 into some segments having two or more longitudinal portions, and some segments that are undivided by longitudinal rib portions 1513. In addition, in the depicted embodiment, alternating groupings of longitudinal rib portions 1513 are laterally offset from adjacent groupings of longitudinal rib portions 1513. In the depicted embodiment, six longitudinal rib portions 1513 are included. In some embodiments, zero, one, two, three, four, five, seven, nine, eight, ten, eleven, twelve, or more than twelve longitudinal rib portions 1513 are included. Any suitable number of groupings of longitudinal rib portions 1513 can be included. Longitudinal ribs 1313 can be made to have any suitable width.

Referring to FIG. 21, an example device 1600 can include a lumenal structure 1605 that includes one or more longitudinal ribs 1613. In the depicted embodiment, three longitudinal ribs 1613 are included. In some embodiments, zero, one, two, four, five, six, seven, eight, nine, ten, eleven, twelve, or more than twelve longitudinal ribs 1613 are included. Such longitudinal ribs 1613 serve to divide overall lumen 1605 into two or more longitudinal portions. Longitudinal ribs 1613 can be made to have any suitable width.

Referring to FIG. 22, an example device 1700 can include a lumenal structure 1705 that includes one or more longitudinal rib portions 1713. Such longitudinal rib portions 1713 serve to divide overall lumen 1705 into some segments having two or more longitudinal portions, and some segments that are undivided by longitudinal rib portions 1713. In the depicted embodiment, three longitudinal rib portions 1713 are included. In some embodiments, zero, one, two, four, five, six, seven, eight, nine, ten, eleven, twelve, or more than twelve longitudinal rib portions 1713 are included. Any suitable number of groupings of longitudinal rib portions 1713 can be included. Longitudinal ribs 1713 can be made to have any suitable width.

Referring to FIG. 23, an example device 1800 can include a lumenal structure 1805 that includes one or more longitudinal rib portions 1813. Such longitudinal rib portions 1813 serve to divide overall lumen 1805 into some segments having two or more longitudinal portions, and some segments that are undivided by longitudinal rib portions 1813. In addition, in the depicted embodiment, alternating groupings of longitudinal rib portions 1813 are laterally offset from adjacent groupings of longitudinal rib portions 1813. In the depicted embodiment, three longitudinal rib portions 1813 are included. In some embodiments, zero, one, two, four, five, six, seven, nine, eight, ten, eleven, twelve, or more than twelve longitudinal rib portions 1813 are included. Any suitable number of groupings of longitudinal rib portions 1813 can be included. Longitudinal ribs 1313 can be made to have any suitable width.

Referring to FIG. 24, an example device 1900 can include a lumenal structure 1905 that includes a plurality of circular pillars 1913. Such circular pillars 1913 serve to constrict lumen 1905 but not prevent all flow of fluid through lumen 1905. Circular pillars 1913 can be made to have any suitable size (e.g., diameter). In the depicted embodiment, circular pillars 1913 are longitudinally aligned in rows.

Referring to FIG. 25, an example device 2000 can include a lumenal structure 2005 that includes a plurality of circular pillars 2013. Such circular pillars 2013 serve to constrict lumen 2005 but not prevent all flow of fluid through lumen 2005. Circular pillars 2013 can be made to have any suitable size (e.g., diameter). In the depicted embodiment, circular pillars 2013 are laterally offset from longitudinally adjacent circular pillars 2013.

Referring to FIG. 26, an example device 2100 can include a lumenal structure 2105 that includes a plurality of ovular pillars 2113. Such ovular pillars 2113 serve to constrict lumen 2105 but not prevent all flow of fluid through lumen 2105. Ovular pillars 2113 can be made to have any suitable size (e.g., length and width). In the depicted embodiment, ovular pillars 2113 are laterally offset from longitudinally adjacent ovular pillars 2113.

Figure 27:
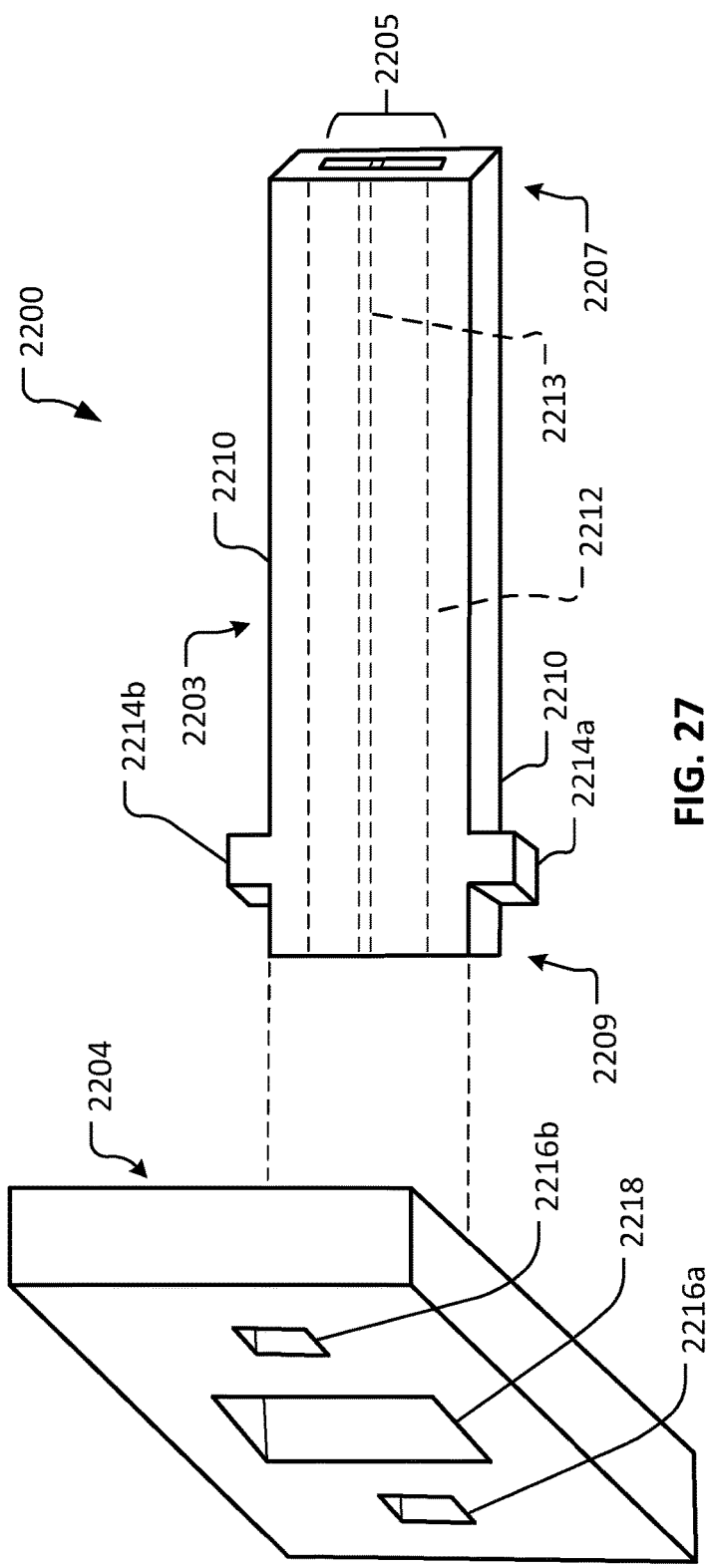
FIG. 27 is an exploded perspective view of another example device in accordance with some embodiments.
Figure 28:
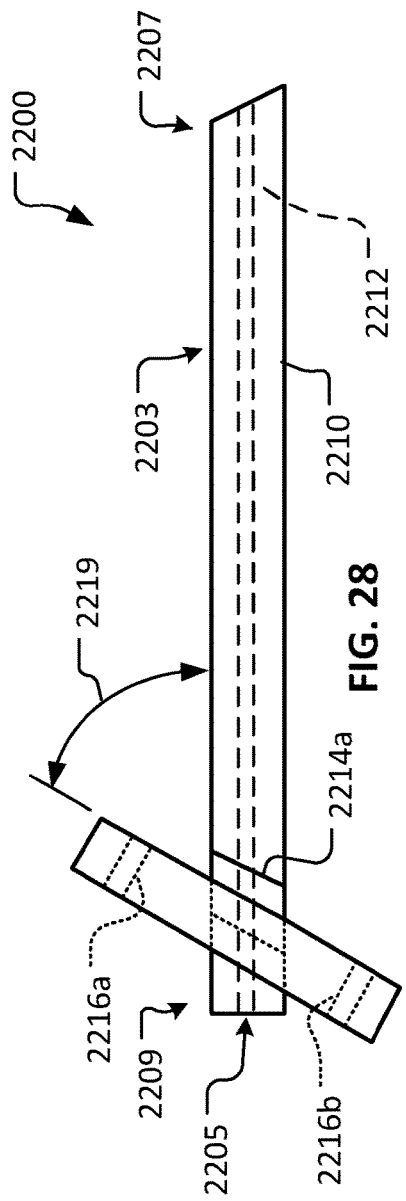
FIG. 28 is a side view of the device of FIG. 27.

Referring to FIGS. 27 and 28, another example device 2200 in accordance with some embodiments provided herein is illustrated. Device 2200 includes a body 2203 that defines a lumen 2205. Body 2203 includes a first end 2207 and a second end 2209. Body 2203 has an external surface 2210, and a lumenal surface 2212. Device 2200 also includes a bolster portion 2204. Bolster portion 2204 can be mated with body 2203. In some cases, second end 2209 of body 2203 can be coupled with receptacle 2218 of bolster portion 2204. In some embodiments, a compression fit (interference fit) exists between body 2203 and bolster portion 2204, such that body 2203 and bolster portion 2204 are held together and effectively function as a monolithic device prior to and after implantation into an eye.

Bolster portion 2204 and body 2203 can be constructed using any of the materials and techniques as described herein in reference to device 1. In addition, in some embodiments, bolster portion 2204, or portions thereof, is made of silicone. In some embodiments, bolster portion 2204, or portions thereof, is made of PET. Device 2200 can be configured and used in any of the manners described herein in reference to device 1.

Bolster portion 2204 provides a stable footing for device 2200 when device 2200 is implanted in an eye. In some cases, at least a portion of bolster portion 2204 contacts the surface of the eye, thereby mechanically stabilizing the device 2200 in relation to the eye. In some cases, bolster portion 2204 can serve to prevent or inhibit tipping of device 2200 in relation to the eye. Other device design features and device use techniques to prevent or inhibit tipping of device 2200 (and the other devices provided herein) in relation to the eye are also envisioned. For example, the inclusion of design features such as barbs, textured surfaces, projections, and other mechanical aspects can be included to prevent or inhibit tipping. Further, in some cases the angle of insertion of the device 200 (and the other devices provided herein) can be selected and/or optimized so prevent or inhibit tipping.

While in the depicted embodiment, bolster portion 2204 is rectangular, in some embodiments, bolster portions with other shapes are used. Such shapes can include, but are not limited to, circles, ovals, squares, parallelograms, and the like. Bolster portion 2219 can be oriented at an angle 2219 in relation to body 2203. In some embodiments, angle 2219 is about a 45° angle. In some embodiments, angle 2219 is within the range from about 40° to about 50°, or from about 35° to about 45°, or from about 45° to about 55°, or from about 30° to about 60°, or from about 20° to about 70°, or from about 10° to about 80°, or from about 0° to about 90°, or greater than about 90°.

In the depicted embodiment, first end 2207 is beveled. In some embodiments, first end 2207 is generally orthogonal in relation to the longitudinal surfaces of external surface 2210. Second end 2209 of the depicted embodiment is not beveled in relation to the longitudinal surfaces of external surface 2210. It should be understood that, in some embodiments of device 2200 and the other devices provided herein, both ends 2207 and 2209 may be beveled (e.g., like first end 2207), both ends 2207 and 2209 may be orthogonal (e.g., like second end 2209), or either one of ends 2207 or 2209 may be beveled while the other one of ends 2207 or 2209 is orthogonal.

In the depicted embodiment, second end 2209 extends beyond bolster portion 2204. In some embodiments, second end 2209 is flush or slightly recessed in relation to bolster portion 2204.

In the depicted embodiment, lumen 2205 includes a longitudinal rib 2213. While in the depicted embodiment, rib 2213 extends continuously from first end 2207 to second end 2209, in some embodiments, rib 2213 may be made of multiple individually shorter segments and/or other arrangements. It should be understood that lumen 2205 may be configured with any of the lumenal constructs provided herein (e.g., FIGS. 15-26, and others), and combinations thereof.

In the depicted embodiment, second end 2209 includes a first flange portion 2214a and a second flange portion 2214b. In some implementations, flange portions 2214a and 2214b contact the surface of the cornea and provide mechanical stabilization of device 2200 in relation to the eye. In addition, in this two-piece construct of device 2200, flange portions 2214a and 2214b engage within recesses of bolster portion 2204 to provide a sturdy mechanical connection therebetween. In the depicted embodiment, flange portions 2214a and 2214b protrude from bolster portion 2204. In some embodiments, flange portions 2214a and 2214b are flush or slightly recessed in relation to bolster portion 2204.

In some embodiments, one or more suture attachment features are included on device 2200 (and the other devices provided herein). In the depicted embodiment, bolster portion 2204 includes a first suture attachment structure 2216a and a second suture attachment structure 2216b. The suture attachment structures 2216a and 2216b are holes in the depicted embodiment. In some embodiments, other types of suture attachment structures can be alternatively or additionally included. While the depicted embodiment includes two suture attachment structures 2216a and 2216b, in some embodiments, zero, one, three, four, or more than four suture attachment structures are included.

One or more portions of external surface 2210 can be configured for enhanced friction with eye tissue (e.g., the cornea or sclera) to improve mechanical stability and/or migration resistance of the device 2200 (and the other devices provided herein) in relation to the eye. In some embodiments, configurations of external surface 2210 can include, but are not limited to, stippling, knurling, cross-hatching, inclusion of one or more barbs, and the like, and combinations thereof. In some embodiments, some such configurations are created by techniques such as, but not limited to, laser machining, chemical etching, 3D printing, photo etching, and the like.

Figure 29:
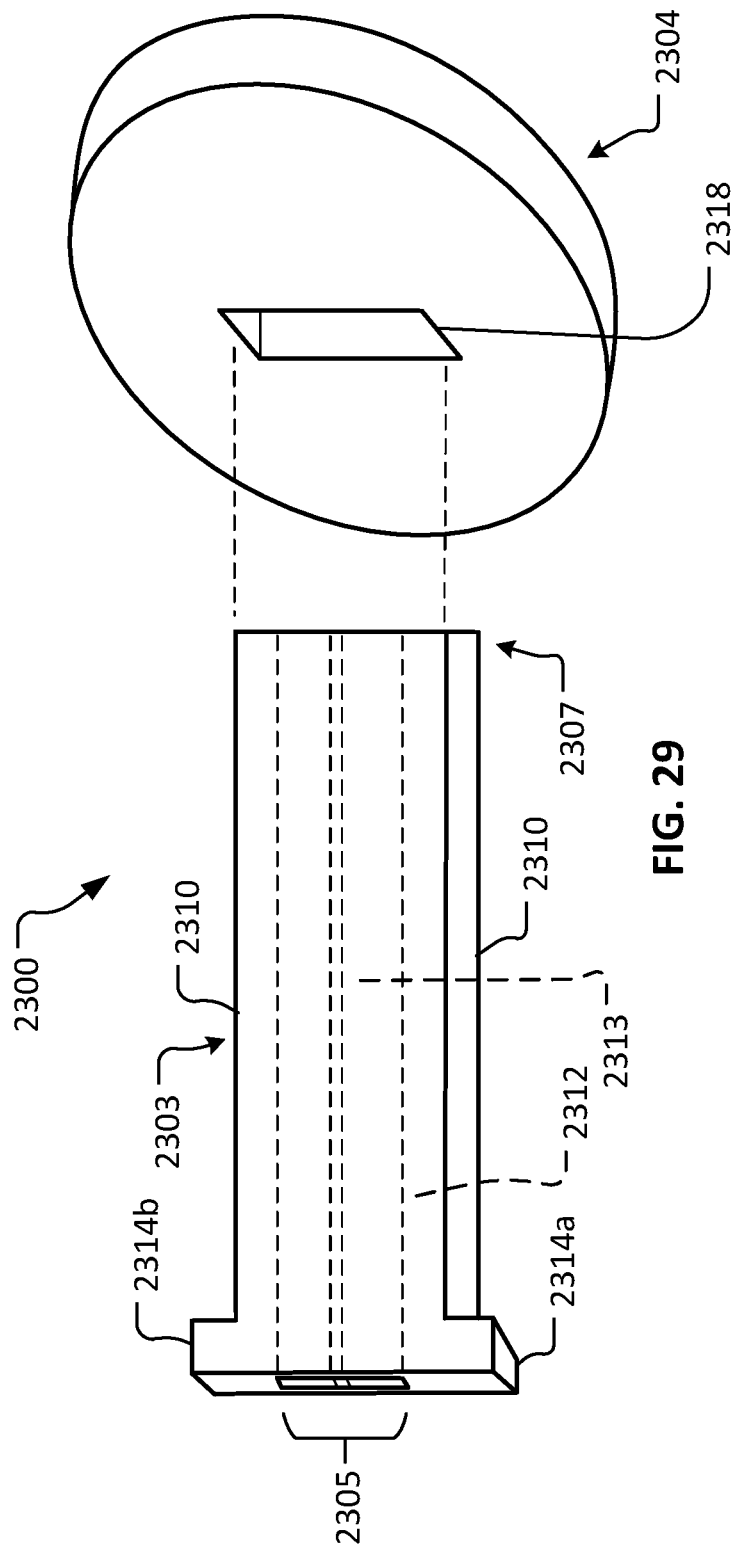
FIG. 29 is an exploded perspective view of another example device in accordance with some embodiments.
Figure 30:
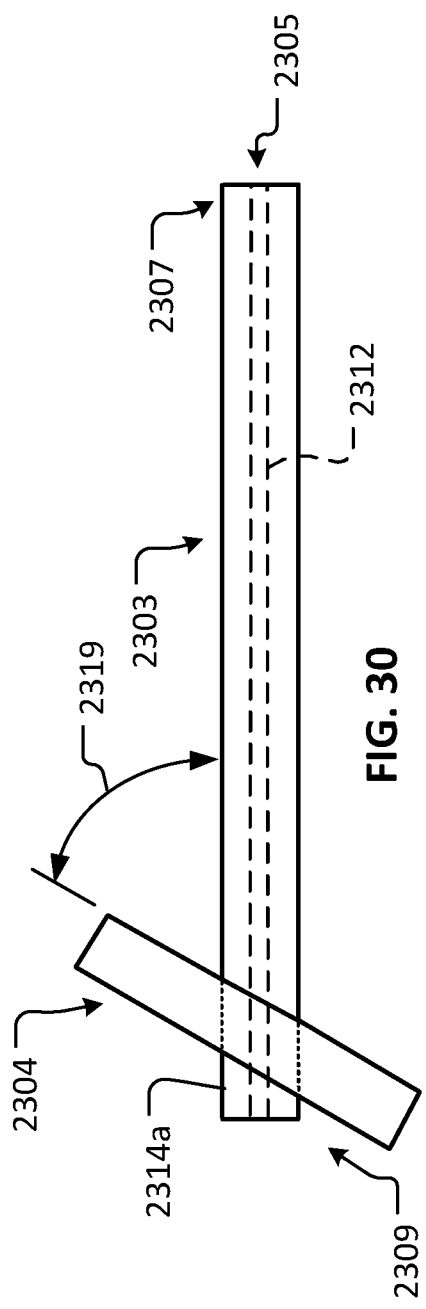
FIG. 30 is a side view of the device of FIG. 29.

Referring to FIGS. 29 and 30, another example device 2300 in accordance with some embodiments provided herein is illustrated. Device 2300 includes a body 2303 that defines a lumen 2305. Body 2303 includes a first end 2307 and a second end 2309. Body 2303 has an external surface 2310 and a lumenal surface 2312. Device 2300 also includes a bolster portion 2304. Bolster portion 2304 can be mated with body 2303. In some cases, body 2303 can be coupled with receptacle 2318 of bolster portion 2304 such that flange portions 2314a and 2314b are positioned in contact with bolster portion 2304. In some embodiments, a compression fit (interference fit) exists between body 2303 and bolster portion 2304, such that body 2303 and bolster portion 2304 are held together and effectively function as a monolithic device prior to and after implantation into an eye.

Bolster portion 2304 and body 2303 can be constructed using any of the materials and techniques as described herein in reference to device 1. In addition, in some embodiments, bolster portion 2304, or portions thereof, is made of silicone. In some embodiments, bolster portion 2304, or portions thereof, is made of PET. Device 2300 can be configured and used in any of the manners described herein in reference to device 1.

Bolster portion 2304 provides a stable footing for device 2300 when device 2300 is implanted in an eye. In some cases, at least a portion of bolster portion 2304 contacts the surface of the eye, thereby mechanically stabilizing the device 2300 in relation to the eye. In some cases, bolster portion 2304 can serve to prevent or inhibit tipping of device 2300 in relation to the eye.

While in the depicted embodiment, bolster portion 2304 is ovular, in some embodiments, bolster portions with other shapes are used. Such shapes can include, but are not limited to, circles, rectangles, squares, parallelograms, and the like. Bolster portion 2319 can be oriented at an angle 2319 in relation to body 2303. In some embodiments, angle 2319 is about a 45° angle. In some embodiments, angle 2319 is within the range from about 40° to about 50°, or from about 35° to about 45°, or from about 45° to about 55°, or from about 30° to about 60°, or from about 20° to about 70°, or from about 10° to about 80°, or from about 0° to about 90°, or greater than about 90°.

In the depicted embodiment, first end 2307 is not beveled. Rather, first end 2307 is generally orthogonal in relation to the longitudinal surfaces of external surface 2310. Second end 2309 of the depicted embodiment is also not beveled in relation to the longitudinal surfaces of external surface 2310. It should be understood that, in some embodiments of device 2300 and the other devices provided herein, both ends 2307 and 2309 may be beveled, both ends 2307 and 2309 may be orthogonal, or either one of ends 2307 or 2309 may be beveled while the other one of ends 2307 or 2309 is orthogonal.

In the depicted embodiment, second end 2309 extends beyond bolster portion 2304. In some embodiments, second end 2309 is flush or slightly recessed in relation to bolster portion 2304.

In the depicted embodiment, lumen 2305 includes a longitudinal rib 2313. While in the depicted embodiment, rib 2313 extends continuously from first end 2307 to second end 2309, in some embodiments, rib 2313 may be made of multiple individually shorter segments and/or other arrangements. It should be understood that lumen 2305 may be configured with any of the lumenal constructs provided herein (e.g., FIGS. 15-26, and others), and combinations thereof.

In the depicted embodiment, second end 2309 includes first flange portion 2314a and second flange portion 2314b. In this two-piece construct of device 2300, flange portions 2314a and 2314b engage with bolster portion 2304 to provide a sturdy mechanical connection therebetween. In the depicted embodiment, flange portions 2314a and 2314b protrude from bolster portion 2304. In some embodiments, flange portions 2314a and 2314b are flush or slightly recessed in relation to bolster portion 2304.

In some embodiments, one or more suture attachment features are included on device 2300 (and the other devices provided herein). In the depicted embodiment, bolster portion 2304 does not include any such suture attachment features. In some embodiments, when bolster portion 2304 is made of silicone, bolster portion 2304 can be pierced by a needle to allow sutures to be threaded through bolster portion 2304 (despite the lack of specific suture attachment features). While the depicted embodiment includes no suture attachment structures, in some embodiments, one, two, three, four, or more than four suture attachment structures are included.

One or more portions of external surface 2310 can be configured for enhanced friction with eye tissue (e.g., the cornea or sclera) to improve mechanical stability and/or migration resistance of the device 2300 (and the other devices provided herein) in relation to the eye. In some embodiments, configurations of external surface 2310 can include, but are not limited to, stippling, knurling, cross-hatching, inclusion of one or more barbs, and the like, and combinations thereof. In some embodiments, some such configurations are created by techniques such as, but not limited to, laser machining, chemical etching, 3D printing, photo etching, and the like.

Figure 31:
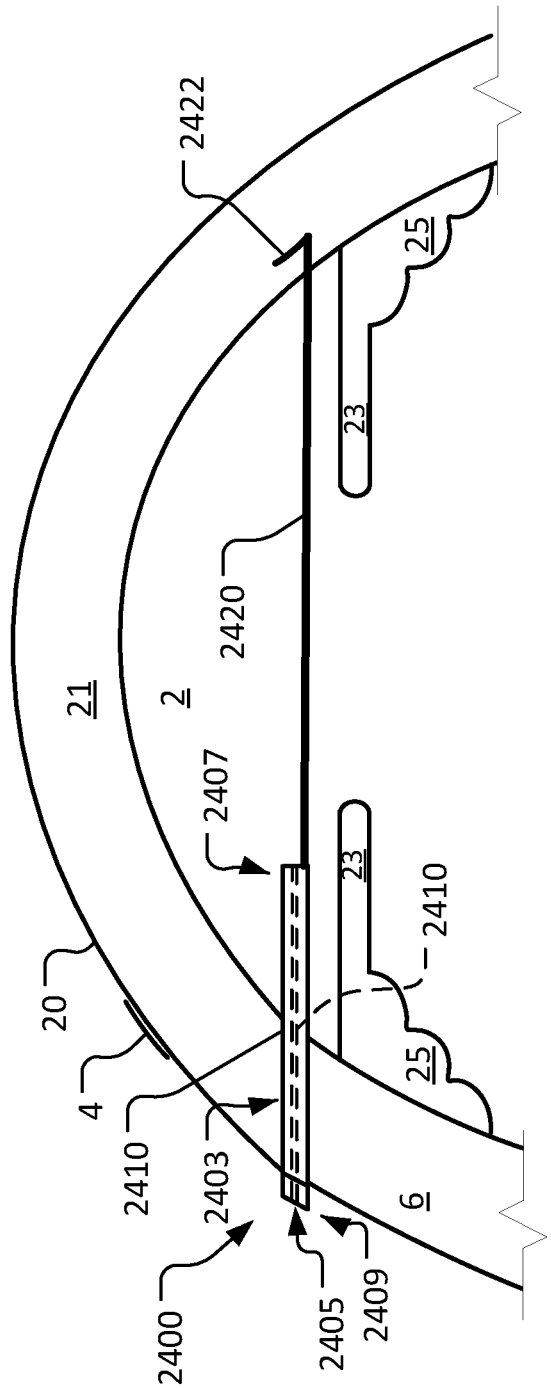
FIG. 31 is a sagittal cross-sectional schematic diagram of an eye with another embodiment of a device illustrative of the devices provided herein implanted in the eye.

Referring to FIG. 31, an example device 2400 is shown implanted in afflicted eye 20 for the purpose of treating glaucoma or dry eye in afflicted eye 20. The depicted anatomical features of eye 20 include anterior chamber 2, sclera 6, tear film 4, iris 23, ciliary body 25, and cornea 21.

Device 2400 includes body 2403 that defines lumen 2405. Body 2403 includes first end 2407 and a second end 2409. Body 2403 has an external surface 2410, and a lumenal surface 2412.

In the depicted embodiment, device 2400 also includes a longitudinal extension member 2420 that is attached to body 2403. An anchor member 2422 is attached to the opposite end of the extension member 2420. Anchor member 2422 can be a structure such as, but not limited to, a barb, a hook, a screw, a clamp, and the like. Anchor member 2422 can be implanted within or attached to cornea 21 or sclera 6. In some cases, extension member 2420 and anchor member 2422 serve to stabilize mechanically device 2400 in relation to eye 20.

In some embodiments, extension member 2420 is a wire member, or another type of elongate member. In some embodiments, extension member 2420 and anchor member 2422 are made of a metallic material such as nitinol or stainless steel. Alternatively or additionally, in some embodiments, extension member 2420 and anchor member 2422 are made of a polymeric material.

Figure 32:
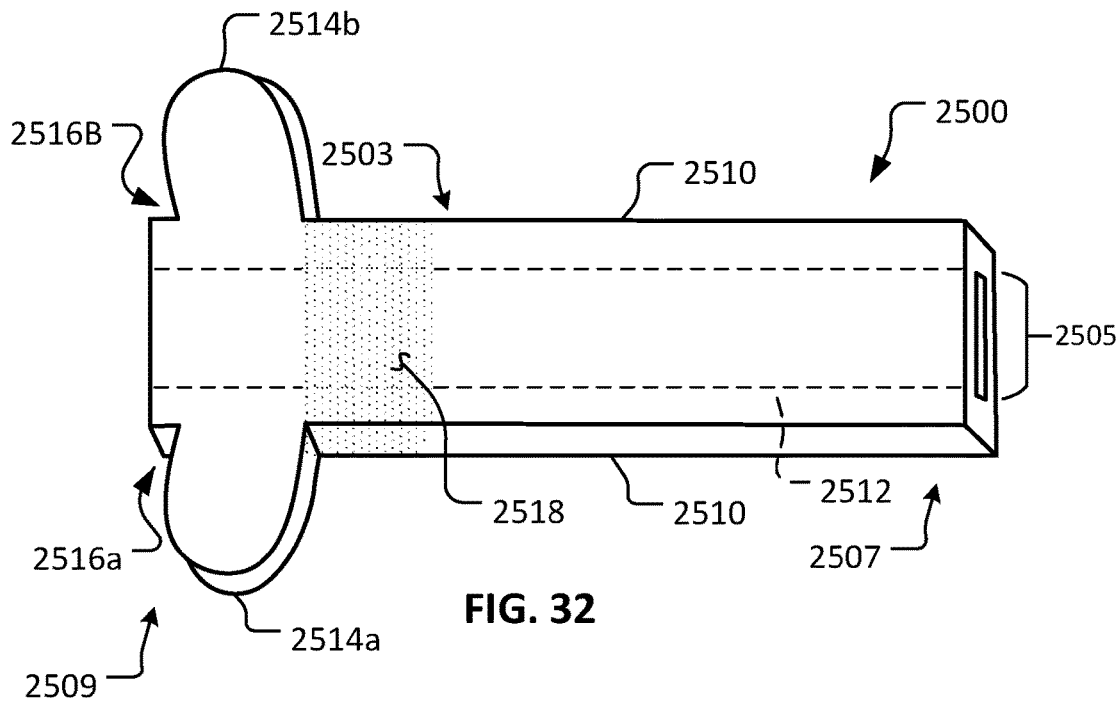
FIG. 32 is a perspective view of another example device in accordance with some embodiments.

Referring to FIG. 32, another example device 2500 in accordance with some embodiments provided herein is illustrated. Device 2500 includes a body 2503 that defines a lumen 2505. Body 2503 includes a first end 2507 and a second end 2509. Body 2503 has an external surface 2510 and a lumenal surface 2512.

Device 2500 can be constructed using any of the materials and techniques as described herein in reference to device 1. Also, device 2500 can be configured and used in any of the manners described herein in reference to device 1.

In the depicted embodiment, first end 2507 is beveled. In some embodiments, first end 2507 is generally orthogonal in relation to the longitudinal surfaces of external surface 2510. Second end 2509 of the depicted embodiment is not beveled in relation to the longitudinal surfaces of external surface 2510. It should be understood that, in some embodiments of device 2500 and the other devices provided herein, both ends 2507 and 2509 may be beveled (e.g., like first end 2507), both ends 2507 and 2509 may be orthogonal (e.g., like second end 2509), or either one of ends 2507 or 2509 may be beveled while the other one of ends 2507 or 2509 is orthogonal.

In the depicted embodiment, lumen 2505 is open continuously from first end 2507 to second end 2509. In some embodiments, lumen 2505 can be configured with any of the other lumenal constructs provided herein (e.g., FIGS. 15-26, and others), and combinations thereof.

In the depicted embodiment, second end 2509 includes a first flange portion 2514a and a second flange portion 2514b. In some implementations, flange portions 2514a and 2514b contact the surface of the cornea and provide mechanical stabilization of device 2500 in relation to the eye. The outer lateral surfaces of flange portions 2514a and 2514b are radiused (contoured) in the depicted embodiment. In some embodiments, the outer lateral surfaces of flange portions 2514a and 2514b are planar and parallel to the longitudinal surfaces of external surface 2510. In some embodiments, the outer lateral surfaces of flange portions 2514a and 2514b are planar and unparallel or askew in relation to the longitudinal surfaces of external surface 2510.

In some embodiments, one or more suture attachment features are included on device 2500 (and the other devices provided herein). In the depicted embodiment, second end 2509 includes a first suture attachment structure 2516a and a second suture attachment structure 2516b. The suture attachment structures 2516a and 2516b are grooves in the depicted embodiment. In some embodiments, other types of suture attachment structures can be alternatively or additionally included. While the depicted embodiment includes two suture attachment structures 2516a and 2516b, in some embodiments, zero, one, three, four, or more than four suture attachment structures are included.

One or more portions of external surface 2510 can be configured for enhanced friction with eye tissue (e.g., the cornea or sclera). Advantageous mechanical stability and/or migration resistance of the device 2500 (and the other devices provided herein) in relation to the eye can be facilitated by such portions. For example, in the depicted embodiment, a surface portion 2518 includes an enhanced texture (roughness) in comparison to other portions of external surface 2510. In the depicted embodiment, surface portion 2518 is a stippled surface. In some embodiments, other types of texturing configurations can be alternatively or additionally included. For example, such texturing configurations can include, but are not limited to, cross-hatching, knurling, inclusion of one or more barbs, and the like, and combinations thereof. In some embodiments, the surface portion 2518 is created by techniques such as, but not limited to, laser machining, chemical etching, 3D printing, photo etching, and the like.

Figure 33:
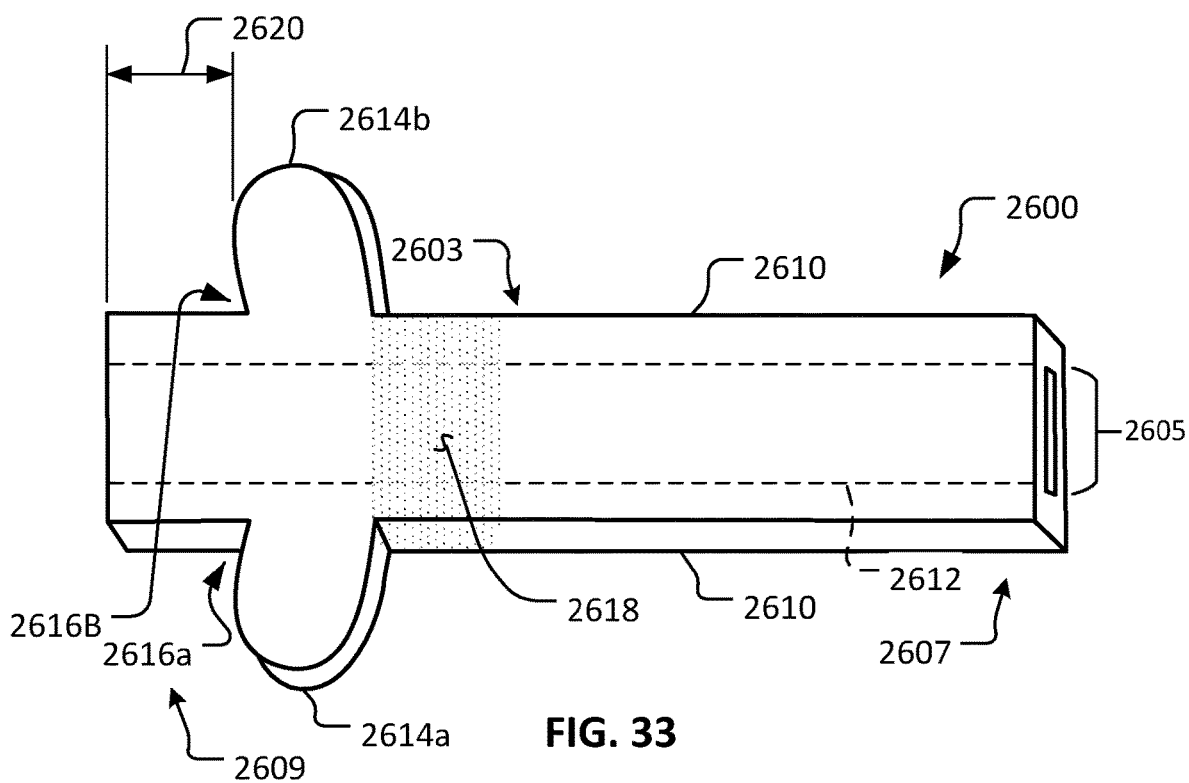
FIG. 33 is a perspective view of another example device in accordance with some embodiments.

Referring to FIG. 33, another example device 2600 in accordance with some embodiments provided herein is illustrated. Device 2600 includes a body 2603 that defines a lumen 2605. Body 2603 includes a first end 2607 and a second end 2609. Body 2603 has an external surface 2610, and a lumenal surface 2612.

Device 2600 can be constructed using any of the materials and techniques as described herein in reference to device 1.

Also, device 2600 can be configured and used in any of the manners described herein in reference to device 1.

In the depicted embodiment, device 2600 is generally configured in the arrangement as device 2500 of FIG. 32. Device 2600 differs from device 2500 in that second end 2609 is extended beyond flange portions 2614a and 2614b by a distance 2620. In some embodiments, distance 2620 is about 300 µm. In some embodiments, distance 2620 is in a range from about 200 µm to about 400 µm, or from about 100 µm to about 500 µm, or from about 0 µm to about 600 µm.

Referring to FIG. 34, example devices 2700 and 2800 can be implanted in an eye 20 that is afflicted with glaucoma or a dry eye condition.

A second method for installing the devices provided herein is as follows. Sometime before installation, the eye is irrigated with 1-5% Betadine solution, and topical antibiotic and non-steroidal anti-inflammatory drops (NSAID) are applied to the operative eye. These can be continued for about one week postoperatively four times a day. The NSAID can help stabilize the blood-aqueous barrier. All embodiments of the device illustrated herein may be inserted under topical anesthesia, possibly supplemented subconjunctivally.

This insertion procedure can be conducted without excising conjunctiva at the site of the anticipated insertion. Approximately 1-2 mm posterior to the limbus, a diamond blade can be used to make a stab incision into the anterior chamber, while held roughly parallel to the iris. The blade can be of a size predetermined to make an opening into the anterior chamber sized appropriately for the introduction of the device. This stab incision can be made gently, but relatively quickly, assiduously avoiding any and all intraocular structures.

The device is next picked up and can be held with a non-toothed forceps. The lips of the stab incision wound may be gaped with a fine, toothed forceps. The pointed tip of the tube element would then be gently pushed through the scleral tract of the stab incision and into the anterior chamber, with the device lying above and parallel to the iris, with the bevel up (i.e., anteriorly). The lateral flanges in the embodiments so configured provide for a definite endpoint to the depth of insertion. For embodiments of the device having a beveled first end, the bevel is oriented anteriorly to minimize the potential for blockage of the lumenal opening by the iris. The scleral barb(s) or other outer surface features (if included) can stabilize the device until the biointegration with the sclera is complete. This biointegration is a function of its porous cellular ingrowth surface, possibly enhanced by adsorbed growth factors and/or grafted extracellular matrix proteins. In some implementations, one or more sutures may be added using the device's suture attachment features to stabilize the device prior to biointegration. For example, a 10-0 nylon suture on a broad spatula needle may be used to suture the device the sclera, providing additional stability to the device until the biointegration is complete. This suture may then be easily removed at a later time if needed. An alternative insertion technique can include having the device pre-loaded into an insertion holder or cartridge, to limit the needed handling of the device by the surgeon. A properly sized sharp blade could be at the leading edge of the inserter, such blade acting also as a guide for implanting the device. Alternatively, the paracentesis can be made with a separate blade, followed by controlled insertion with an inserter.

After insertion of the device, an ocular shield can be placed over the eye. The implanted device can bio-integrate with the sclera, thereby reducing the risks of infections such as tunnel infection.

Referring to FIG. 35, eye 20 is shown after devices 2700 and 2800 have been implanted for a period of approximately two weeks. The end portions of devices 2700 and 2800 have not been overgrown with conjunctival tissue. Hence, the lumens of devices 2700 and 2800 are patent and can function to reduce IOP to treat glaucoma and provide moisture to a dry eye, thereby treating both glaucoma and a dry eye condition in a safe and effective manner. Devices 2700 and 2800 can be suitable for use in monitoring aqueous humor (such as monitoring glucose in aqueous humors) by providing access to aqueous humor by a monitoring device.

Referring to FIG. 36, eye 20 is shown after devices 2700 and 2800 have been implanted for a period of approximately one month. The end portions of devices 2700 and 2800 still have not been overgrown with conjunctival tissue. Hence, the lumens of devices 2700 and 2800 are patent and can function to provide access to aqueous humor for monitoring, to reduce TOP to treat glaucoma and to provide moisture to a dry eye, thereby treating both glaucoma and a dry eye condition in a safe and effective manner. In addition, the photo shows that the prior irritation (redness) of the tissue has subsided. Hence, devices 2700 and 2800 have been successfully integrated by the patient in this example.

Prevention of conjunctival tissue overgrowth to sustain patency of the device's lumen has been found to be effected by a number of various design factors such as, but not limited to, material selection, coatings, physical distance and geometry of the projection of the device from the surface of the eye, and the angle of the projecting end relative to the eye. For example, from animal experimentation, the relationships between time and projection distance (distance from the eye's surface to the end of the device) shown in Table 1 below have been observed.

TABLE 1

Amount of Conjunctival Overgrowth

| Projection Distance | 1 Week after Implantation | 2 Weeks after Implantation | 1 Month after Implantation | 2 Months after Implantation |
|---|---|---|---|---|
| 200 µm | none | partial | full | full |
| 800 µm | none | none | none | none |

Figure 37:
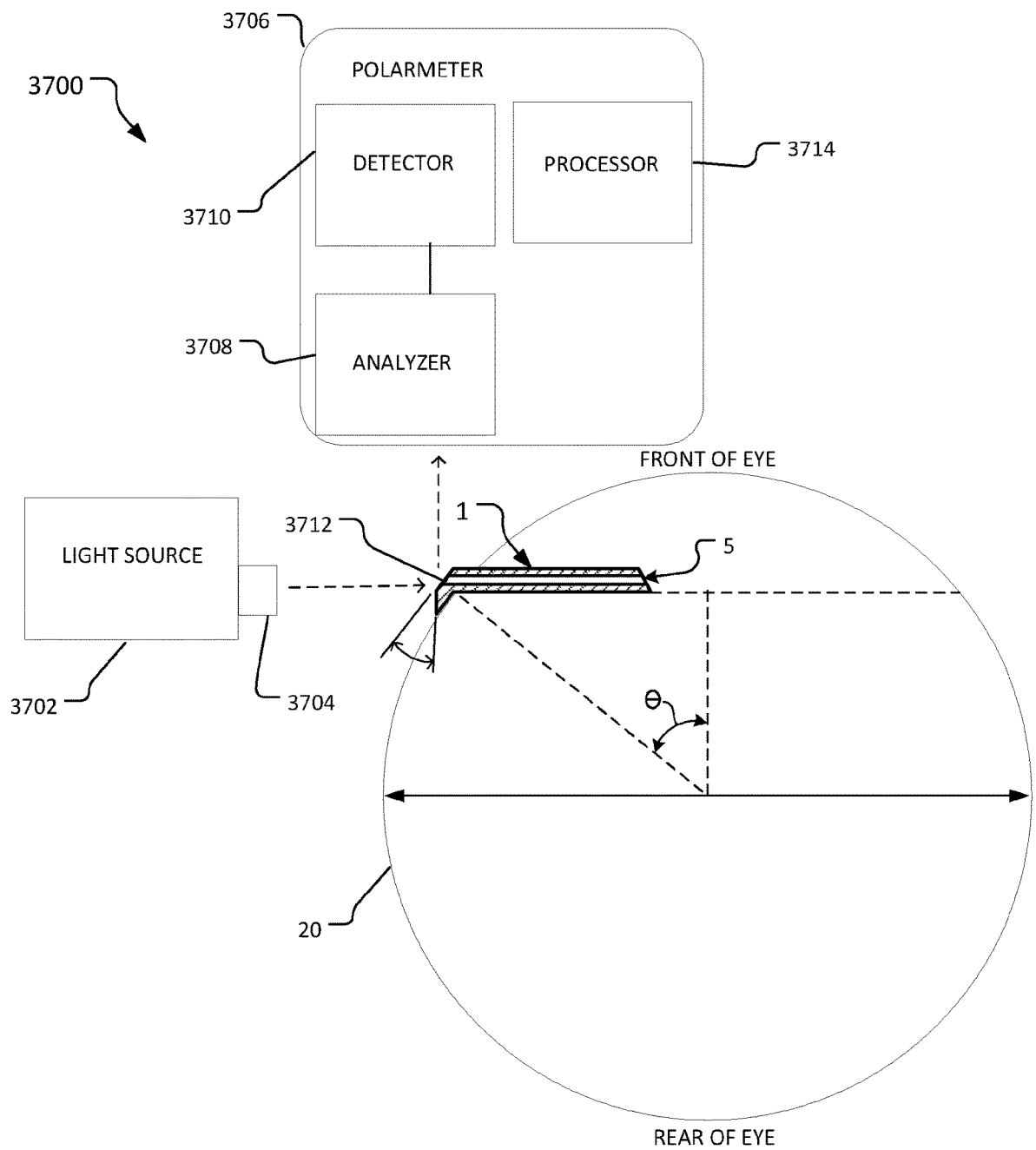
FIG. 37 is a schematic drawing of a sagittal cross-section of an eye and a system for measuring analyte concentration in aqueous humor of the eye.

Referring to FIG. 37, system 3700 is a system for measuring analyte concentration, such as measuring glucose. System 3700 will be described with respect to monitoring glucose though, in some embodiments, system 3700 can monitor an analyte other than glucose where applicable for the application. Examples of analytes that can be monitored in aqueous humor as described herein include, without limitation, glucose, glutathione, SGOT (serum glutamic-oxaloacetic transaminase), albumin, leptin, fibrinogen, IL-8 (interleukin 8), C reactive protein, and erythropoietin. In some cases, two or more (e.g., three, four, five, six, or more) different analytes can be monitored in aqueous humor as described herein.

System 3700 can include device 1, light source 3702 having polarizer 3704, and polarimeter 3706 having analyzer 3708 and detector 3710. Device 1 (and the devices in FIGS. 38-43) is representative here of any of the implantable devices described above. It should be understood that any of the device materials, constructs, shapes, structures, features, etc., and combinations and sub-combinations thereof, as described above can be used in the systems of FIGS. 37-43.

In some embodiments, light source 3702 can be a laser source, polarizer 3704 can be polarized laser light, and detector 3710 can be an optical detector. Light source 3702 can provide a beam of coherent photons, whose angle of polarization can be controlled at light source 3702 during and/or after transmission. In some embodiments, the beam of coherent photons can be incident on the aqueous humor of eye 20. The molecules in the aqueous humor can be enantiomers, which exhibit chirality. This property of the aqueous humor can alter the angle of polarization in the scattered beam of coherent photons.

Light source 3702 can project light (such as a monochromatic light) through polarizer 3704 to be polarized and projected as a polarized beam on exterior portion 3712 of device 1. Aqueous humor can pass from eye 20 through lumen 5 to an exterior of eye 20 and device 1 as described above. Exterior portion 3712 can be reflective. Therefore, polarized light projected on exterior portion 3712 can pass through the aqueous humor to be reflected by exterior portion 3712 to polarimeter 3706. After passing through the aqueous humor and being reflected to polarimeter 3706, analyzer 3708 can rotate for detecting the angle of polarization. When analyzer 3708 is rotated to the proper angle, an amount of light that is at or near the maximum amount of light will pass through and shine onto detector 3710. Processor 3714 can then analyze the results to calculate glucose level in the aqueous humor, and consequently, glucose level in the blood.

The angle of this rotation can depend linearly on optical path-length, concentration of the chiral species, and a constant for the species known as the specific rotation; which can be expressed as $\phi = \alpha_\lambda LC$ where $\alpha_\lambda$ is the specific rotation in $° \, dm^{-1} \, (g/ml)^{-1}$ at wavelength $\lambda$, L is the path length in dm, and C is the concentration in g/mL. Glucose in the body can be dextrorotatory (rotates light in the right-handed direction) and have a specific rotation of $+52.6° \, dm^{-1} \, (g/ml)^{-1}$ at the sodium D-line of 589 nm. Typically, $\alpha_\lambda$ for glucose decreases with increasing wavelength across the visible spectrum and exhibits a rise in magnitude near optical absorption bands of a particular molecule. Intensity of light incident on detector 3710 can be proportional to the square of the amplitude of the E-field of light passing through analyzer 3708 which can be proportional to the sine of the angle $\phi$ by which the light was rotated in the aqueous humor. For small rotation angles, this can be $E^2 \propto \sin^2 \phi = 1 - \cos 2\phi \approx 2\phi$.

In some embodiments, system 3700 can be modified to include one or more additional or different components than described above. For example, in some embodiments system 3700 can include polarimeter 3706 as described herein and in other embodiments system 3700 can include a different polarimeter suitable for the application. In some embodiments, the system 3700 can include a spectrometer (such as a Raman spectrometer for example) or a refractometer.

System 3700 can supply aqueous humor exterior to eye 20 to allow for measurement of analyte concentration (such as glucose concentration) in the aqueous humor. By measuring glucose in aqueous humor with relatively low scattering properties (as opposed to measuring in a substance such as blood with relatively high scattering properties), glucose levels can be measured relatively accurately. By including device 1 (or another suitable device such as those described herein) to deliver aqueous humor exterior of eye 20, light need not necessarily be directed into eye 20 by light source 3702. This can allow aqueous humor, a substance typically found interior to eye 20, to be measured exterior to eye 20.

Figure 38:
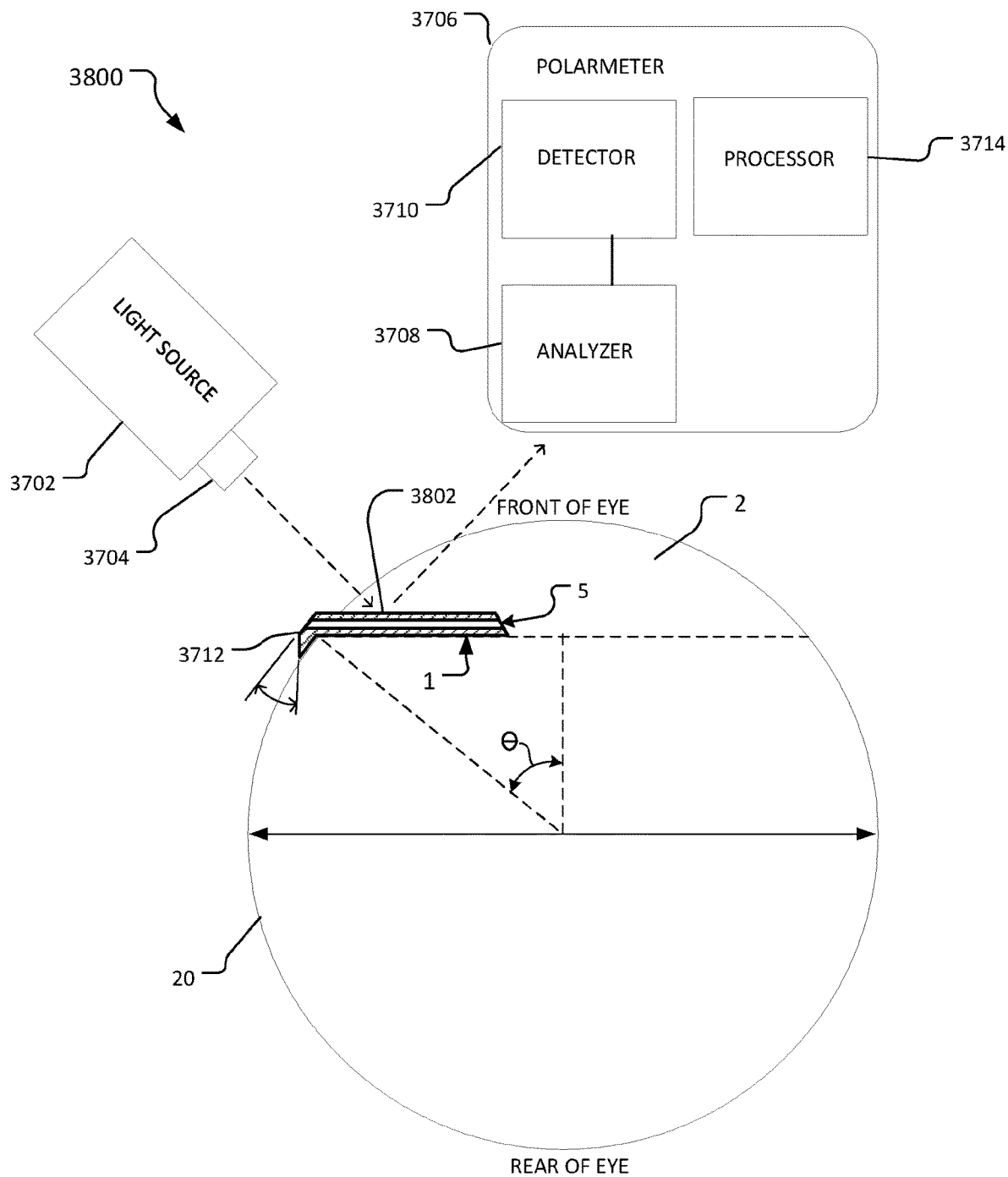
FIG. 38 is a schematic drawing of a sagittal cross-section of an eye and another embodiment of a system for measuring analyte concentration in aqueous humor of the eye.

Referring to FIG. 38, system 3800 is another system for measuring analyte concentration, such as measuring glucose. System 3800 can be constructed and can function similar to system 3700 except as described herein. For example, system 3800 can also include device 1, light source 3702 having polarizer 3704, and polarimeter 3706 having analyzer 3708 and detector 3710. Device 1 can have exterior portion 3712 as well as interior portion 3802. Exterior portion 3712 can be positioned exterior to eye 20 when device 1 is positioned in eye 20 and interior portion 3802 can be positioned interior of eye 20 when device 1 is positioned in eye 20. In some embodiments, interior portion 3802 can include that portion of device 1 extending through sclera 6 (shown, for example, in FIG. 1). In some embodiments, interior portion 3802 can include that portion of device 1 extending into anterior chamber 2.

System 3800 can be configured such that light source 3702 can project light (such as a monochromatic light) through polarizer 3704 to be polarized and projected as a polarized beam through cornea 20 onto interior portion 3802 of device 1. Interior portion 3802 can be reflective. Therefore, polarized light projected on interior portion 3802 can pass through the aqueous humor in eye 20 to be reflected by the interior portion 3802 to polarimeter 3706. After passing through the aqueous humor and being reflected to polarimeter 3706, analyzer 3708 can rotate for detecting the angle of polarization. When analyzer 3708 is rotated to the proper angle, an amount of light that is at or near the maximum amount of light will pass through and shine onto detector 3710. Processor 3714 can then analyze the results to calculate glucose level in the aqueous humor, and consequently, glucose level in the blood.

System 3800 can measure analyte concentration (such as glucose concentration) in the aqueous humor while the aqueous humor is still in eye 20. By measuring glucose in aqueous humor with relatively low scattering properties (as opposed to measuring in a substance such as blood with relatively high scattering properties), glucose levels can be measured relatively accurately. Using device 1 to reflect the light can allow for polarimeter 3706 to better measure glucose concentration (as compared, for example, to attempting to measure glucose concentration in aqueous humor in eye 20 with no reflective device 1). In some embodiments, light from light source 3702 needs to travel only a relatively short distance through eye 20 before being reflected and traveling a relatively short distance through eye 20 back out to polarimeter 3706. This can provide a relatively efficient and effective mechanism for measuring glucose concentration. This can be particularly beneficial for users suffering from glaucoma and/or dry eyes, as device 1 can perform multiple functions.

Figure 39:
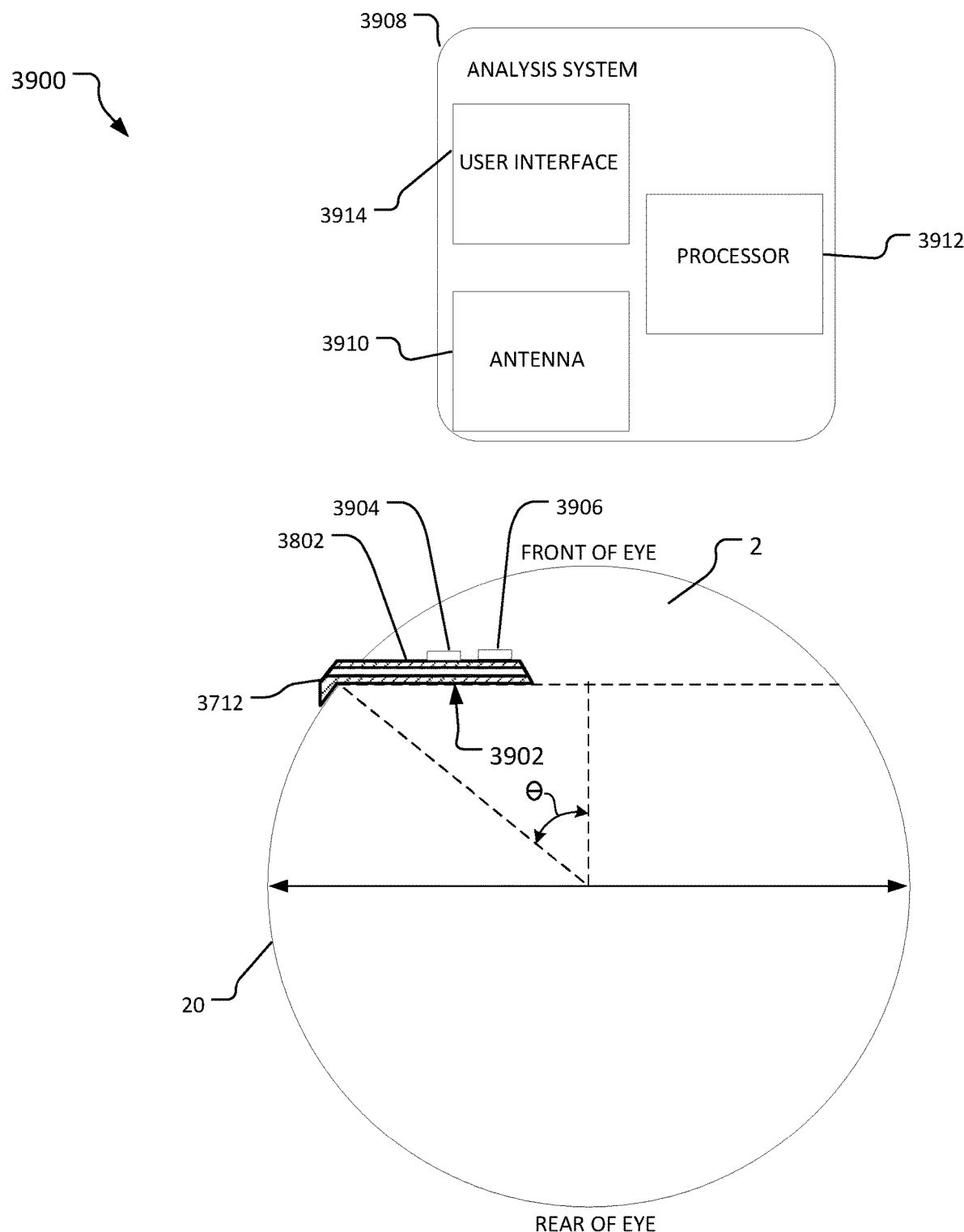
FIG. 39 is a schematic drawing of a sagittal cross-section of an eye and another embodiment of a system for measuring analyte concentration in aqueous humor of the eye.

Referring to FIG. 39, system 3900 is another system for measuring analyte concentration, such as measuring glucose. System 3900 can include device 3902, which can be similar to device 1 or other devices described above, except that device 3902 can also include antenna 3904 and sensor 3906. Sensor 3906 can be positioned on interior portion 3802 of device 3902 so as to be positioned in aqueous humor of eye 20 when device 3902 is implanted in eye 20. Sensor 3906 can be mounted on device 3902 in a location and configuration so as to be in contact with aqueous humor for measuring analyte concentration in the aqueous humor, such as measuring glucose. In some embodiments, sensor 3906 can be mounted on device 3902 in a location that is in contact with aqueous humor of eye 20 but is substantially isolated from tears from eye 20. Glucose concentration in tears can vary due to factors such as stress of the user. Thus, sensing aqueous humor instead of tears can be a more consistent and reliable indicator of the user's actual glucose concentration in his or her blood.

In some embodiments, device 3902 can include antenna 3904 connected in communication with sensor 3906. For example, antenna 3904 can be connected to sensor 3906 via a connecting wire. In some embodiments, antenna 3904 can be integrally formed with sensor 3906. Antenna 3904 can communicate data (such as glucose concentration) sensed via sensor 3906 to analysis system 3908.

Analysis system 3908 can include antenna 3910 which can wirelessly communicate with antenna 3904 of device 3902, processor 3912 which can receive and process data sensed by sensor 3902, and user interface 3914 which can display or otherwise communicate information to a user. For example, sensor 3906 can sense glucose concentration in aqueous humor of eye 20. Device 3902 can transmit glucose concentration data to analysis system 3908 via antennas 3904 and 3910. Processor 3912 can then control user interface 3914 to display information to a user, such as displaying the glucose concentration data directly via user interface 3914 or displaying information that was generated as a function of the sensed glucose concentration data.

Sensor 3906 can be one of a variety of sensors suitable for the application. In some embodiments, for example, sensor 3906 can be a biosensor that generates electrical current that is a function of sensing glucose in aqueous humor. Generated current can modify impedance of antenna 3904, causing antenna 3910 to sense a signal from antenna 3904 that is a function of sensed glucose concentration in the aqueous humor.

In some embodiments, sensor 3906 can be a voltage biosensor that varies its voltage as a function of sensing glucose in aqueous humor. Change in voltage can modify impedance of antenna 3904, causing antenna 3910 to sense a signal from antenna 3904 that is a function of sensed glucose concentration in the aqueous humor.

In some embodiments, sensor 3906 can be a charge biosensor that varies its charge as a function of sensing glucose in aqueous humor. Change in charge can modify impedance of antenna 3904, causing antenna 3910 to sense a signal from antenna 3904 that is a function of sensed glucose concentration in the aqueous humor.

In some embodiments, sensor 3906 can be a capacitance biosensor that varies its capacitance as a function of sensing glucose in aqueous humor. Change in capacitance can modify impedance of antenna 3904, causing antenna 3910 to sense a signal from antenna 3904 that is a function of sensed glucose concentration in the aqueous humor.

In some embodiments, sensor 3906 can be an impedance biosensor that varies its impedance as a function of sensing glucose in aqueous humor. Change in impedance of sensor 3906 can modify impedance of antenna 3904, causing antenna 3910 to sense a signal from antenna 3904 that is a function of sensed glucose concentration in the aqueous humor.

In some embodiments, sensor 3906 can be a fluorescence biosensor, such as a fluorescent glucose biosensor, that relays glucose concentration in aqueous humor via fluorescence. In some embodiments, the sensor 3906 can include a fluorescent protein that fluoresces as a function of glucose concentration in aqueous humor as well as a detecting subsystem which detects fluorescence of the fluorescent protein. Antenna 3904 can transmit detected fluorescence to antenna 3910 of analysis subsystem 3908.

In some embodiments, sensor 3906 can be a fluorescence biosensor without requiring a detection subsystem to be included on device 3902. For example, sensor 3906 can include a fluorescent protein that fluoresces as a function of glucose concentration in aqueous humor, while the detecting subsystem which detects fluorescence of the fluorescent protein can be external to eye 20. For example, an optical detector can be used to detect fluorescence of the fluorescent protein in the aqueous humor by line of sight to the sensor 3906. In some embodiments, the analysis system 3908 can include an optical detector for receiving and detecting fluorescence of the sensor 3906. By monitoring change of fluorescence intensity at a wavelength around a peak of fluorescence of the fluorescent protein in sensor 3906, an amount of fluorescence can vary as a function of glucose concentration in the aqueous humor of eye 20. Processor 3912 can then determine blood glucose level as a function of glucose concentration in the aqueous humor, and consequently, as a function of sensed fluorescence.

In some embodiments, analysis system 3908 can be a device configured for use by medical personnel. In some embodiments, analysis system 3908 can be a device configured for use by a patient or user in regular (e.g. daily) use. By configuring analysis system 3908 for regular use by the patient, that patient can regularly monitor his or her own glucose level without requiring repeated skin penetration with each measurement. In some embodiments, analysis system 3908 can be integrated with and/or connectable to a set of eyeglasses (such as, for example, reading glasses or sunglasses). By connecting or mounting analysis system 3908 to a set of eyeglasses, analysis system 3908 can be positioned in proximity to device 3902 to facilitate operation of analysis system 3908 in conjunction with device 3902. For example, in embodiments in which analysis system 3908 includes antenna 3910 and device 3712 includes antenna 3904, use of eyeglasses can position analysis system 3908 in a location configured for allowing wireless communication at low power. Moreover, in embodiments in which analysis system 3908 includes an optical detector and device 3902 include sensor 3906 having a fluorescent protein, the eyeglasses can position the analysis system 3908 in a position configured for optically detecting fluorescence of sensor 3906. In some embodiments, the analysis system 3908 can be part of and/or connected to a mobile computing device, such as a smartphone or tablet.

In some embodiments, systems 3700 and 3800 (shown in FIGS. 37 and 38) can be configured for use by medical personnel when device 1 implanted in a patient. In some embodiments, systems 3700 and 3800 (including device 1, polarimeter 3706, and light source 3702) can be configured for use by a patient or user in regular (e.g. daily) use. By configuring systems 3700 and 3800 for regular use by the patient, that patient can regularly monitor his or her own glucose level without requiring repeated skin penetration with each measurement (such as to draw blood). In some embodiments, light source 3702 and polarimeter 3706 can be integrated with and/or connectable to a set of eyeglasses (such as, for example, reading glasses or sunglasses). By connecting or mounting light source 3702 and polarimeter 3706 to a set of eyeglasses, light source 3702 and polarimeter 3706 can be positioned in proximity to device 1 to facilitate operation of light source 3702 and polarimeter 3706 in conjunction with device 1. For example, the eyeglasses can position light source 3702 and polarimeter 3706 in a position corresponding to device 1 for optically detecting polarimetry of glucose in aqueous humor. In some embodiments, the eyeglasses can position light source 3702 and polarimeter 3706 in a position aligned with exterior portion 3712 of device 1 for optically detecting polarimetry of glucose in aqueous humor that has exited eye 20 through device 1. In some embodiments, the eyeglasses can position light source 3702 and polarimeter 3706 in a position aligned with interior surface 3802 of device 1 for optically detecting polarimetry of glucose in aqueous humor that remains in eye 20.

In some embodiments, systems 3700 and 3800 need not necessarily include eyeglasses but can still position light source 3702 and polarimeter 3706 in a position corresponding to device 1 for optically detecting polarimetry of glucose in aqueous humor. For example, systems 3700 and 3800 can include another suitable structure for positioning light source 3702 and polarimeter 3706 with respect to eye 20 and device 1 utilizing features of a user's face in a manner similar to eyeglasses without actually being eyeglasses.

Figure 40:
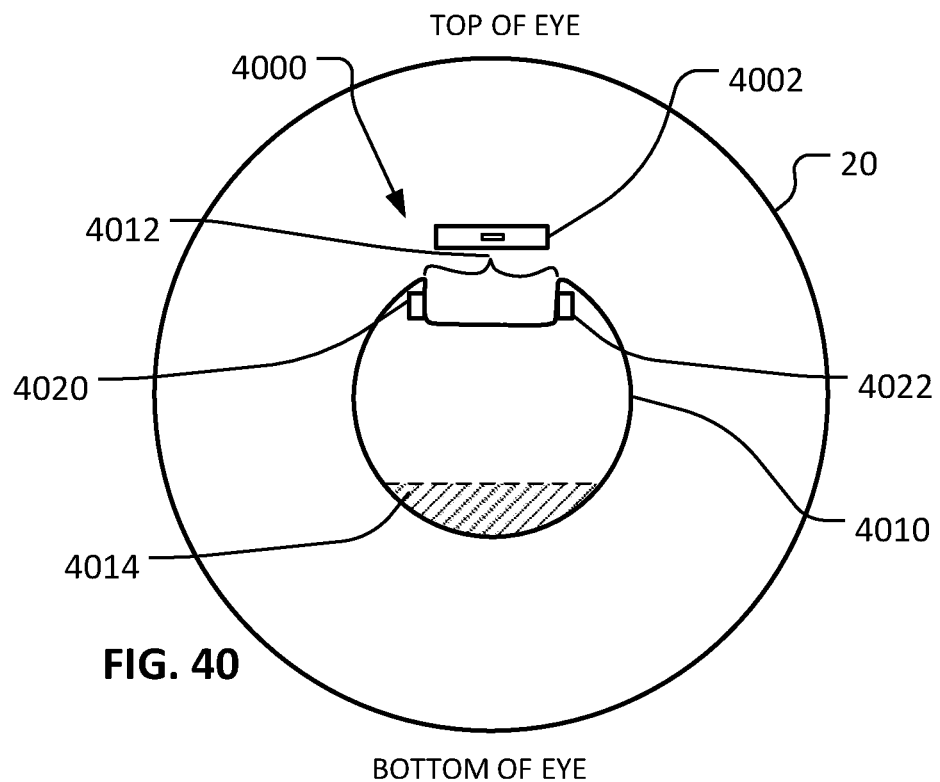
FIG. 40 is a front view of an eye that includes an example implanted lumenal device and that is wearing an example contact lens that has been adapted to detect an analyte of aqueous humor exuded through the lumenal device.

Referring to FIG. 40, system 4000 is another system for measuring analyte concentration in aqueous humor of an eye 20. For example, in one non-limiting example, system 4000 is used to measure glucose concentration in aqueous humor of eye 20. Other types of analytes can be additionally or alternatively measured using system 4000. Such analytes can include but are not limited to, potassium, sodium, bicarbonate, key tones, warfarin, pharmacological agents, and the like, and combinations thereof.

System 4000 includes a device 4002 that can be similar to device 1 or any other implantable lumenal device described herein. In addition, system 4000 includes a generally transparent contact lens 4010 worn in contact with eye 20.

In the depicted embodiment, contact lens 4010 defines a well 4012 that serves as a holding area for aqueous humor that is exuded from device 4002 as described above. As shown, in some embodiments well 4012 is a notch in the perimeter of contact lens 4010. Well 4012 is generally rectangular in the depicted embodiment, but well 4012 can be other shapes such as semi-circular, semi-ovular, triangular, and the like. In some embodiments, well 4012 is an opening defined by contact lens 4010. In some embodiments, contact lens 4010 may define one or more channels as an alternative to, or in additional to, well 4012.

Optionally, contact lens 4010 can include a ballast region 4014 (shown in cross-hatch only to indicate a particular portion of contact lens 4010, but not to indicate non-transparency). Ballast region 4014 is a localized area of contact lens 4010 that is comparatively heavier than other areas of contact lens 4010. Accordingly, ballast region 4014 can serve to orient contact lens 4010 in relation to eye 20 generally as shown (i.e., with the ballast region 4014 located on the bottom of contact lens 4010).

In some embodiments, ballast area 4014 is located in a known orientation in relation to well 4012 (e.g., ballast area 4014 is located opposite of well 4012 in the depicted embodiment). Accordingly, orientation of contact lens 4010, as determined or influenced by ballast region 4014, also serves to orient well 4012 in a desired location relative to eye 20. For example, in the depicted embodiment the ballast area 4014 serves to orient well 4012 in alignment just below device 4002. Accordingly, aqueous humor exuded through device 4002 will tend to collect in well 4012.

Various types of sensor systems for measuring analytes in aqueous humor can be included as part of contact lens 4010. For example, any of the sensors described above in reference to FIGS. 37-39 can be included. In the depicted embodiment, a polarizer 4020 and a polarimeter 4022 are included as part of contact lens 4010 (e.g., as described above in reference to FIGS. 37 and 38).

In some embodiments, contact lens 4010 can also include a system for wirelessly transmitting signals indicative of the detected analyte concentration. For example, contact lens 4010 can include one or more components such as, but not limited to, a controller, a capacitor, a power source, an antenna, an energy transfer antenna, communications circuitry, and the like. Such signals wirelessly transmitted can be received by a device of the user such as, but not limited to, a smart phone, an insulin pump, a remote display device, a wearable device (e.g., eyeglasses) and the like. In some embodiments, an insulin pump is operated in a closed-loop fashion using wirelessly transmitted data from system 4000 as feedback.

Figure 41:
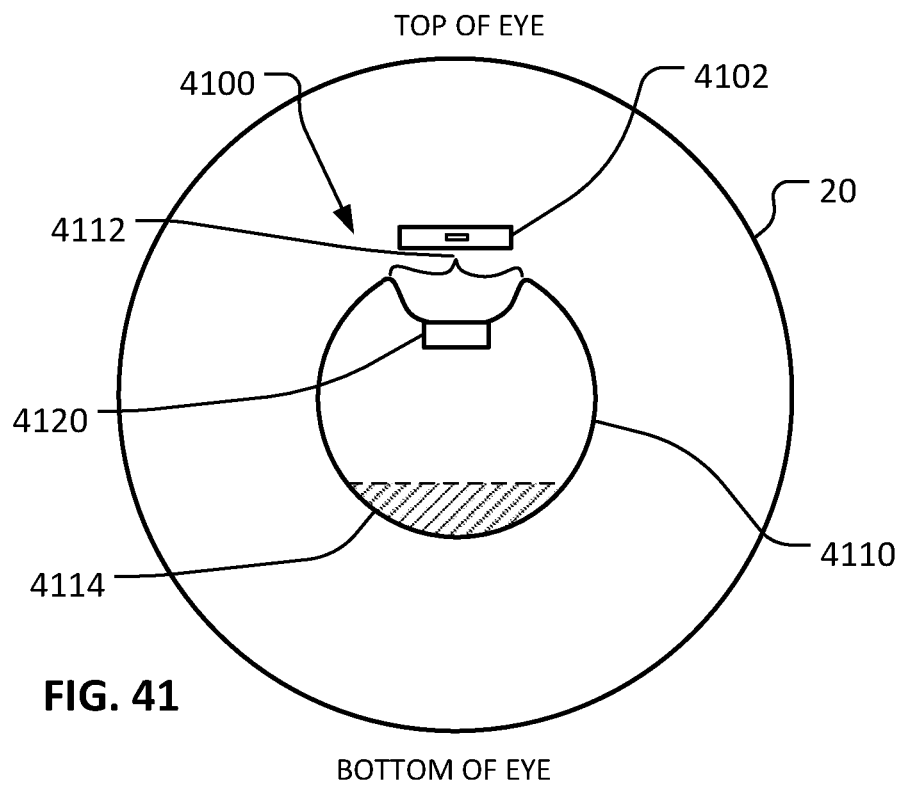
FIG. 41 is a front view of an eye that includes an example implanted lumenal device and that is wearing another example contact lens that has been adapted to detect an analyte of aqueous humor exuded through the lumenal device.

Referring to FIG. 41, system 4100 is another system for measuring analyte concentration in aqueous humor of an eye 20. For example, in one non-limiting example, system 4100 is used to measure glucose concentration in aqueous humor of eye 20. Other types of analytes can be additionally or alternatively measured using system 4100.

System 4100 includes a device 4102 that can be similar to device 1 or any other implantable lumenal device described herein. In addition, system 4100 includes a generally transparent contact lens 4110 worn in contact with eye 20.

In the depicted embodiment, contact lens 4110 defines a generally semi-circular well 4112 that serves as a holding area for aqueous humor that is exuded from device 4102 as described above. Contact lens 4110 also includes an optional ballast region 4014 (shown in cross-hatch only to indicate a particular portion of contact lens 4110, but not to indicate non-transparency).

Contact lens 4110 also includes a sensor 4120 for measuring analytes in the aqueous humor. Sensor 4120 can be, for example, any of the sensors described above in reference to FIGS. 37-39. In some embodiments, sensor 4120 can be, without limitation, an electrochemical enzymatic glucose sensor, or an electrochemical non-enzymatic glucose sensor, or a fluorescent glucose biosensor, or a chemFET sensor, and the like.

In some embodiments, contact lens 4110 can also include a system for wirelessly transmitting signals indicative of the detected analyte concentration. For example, contact lens 4110 can include one or more components such as, but not limited to, a controller, a capacitor, a power source, an antenna, an energy transfer antenna, communications circuitry, and the like. Such signals wirelessly transmitted can be received by a device of the user such as, but not limited to, a smart phone, an insulin pump, a remote display device, a wearable device (e.g., eyeglasses) and the like. In some embodiments, an insulin pump is operated in a closed-loop fashion using wirelessly transmitted data from system 4100 as feedback.

Figure 42:
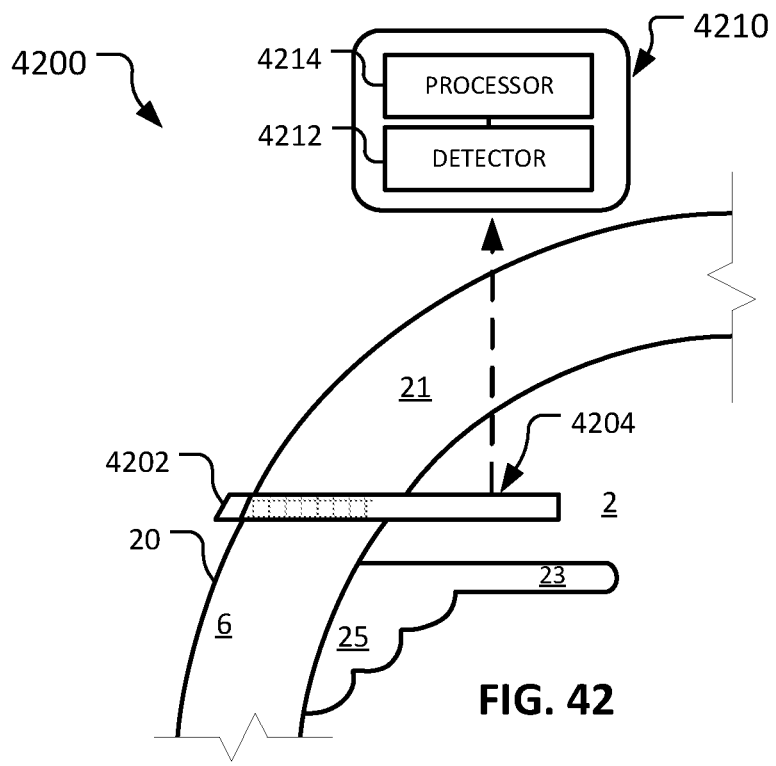
FIG. 42 is a sagittal cross-sectional schematic diagram of an eye that includes an example implanted device that has been adapted to indicate the presence of an analyte of aqueous humor in contact with the device.

Referring to FIG. 42, system 4200 is another system for measuring analyte concentration in aqueous humor of an eye 20. For example, in one non-limiting example, system 4200 is used to measure glucose concentration in aqueous humor of eye 20. Other types of analytes can be additionally or alternatively measured using system 4200.

System 4200 includes a device 4202 and an analysis system 4210. Device 4202 can be similar to device 1 or any other implantable lumenal device described herein. In some embodiments, device 4202 does not include a lumen. Alternatively, in some embodiments, device 4202 includes a lumen as described elsewhere herein. In other words, a lumen in the device 4202 of system 4200 is optional. That is the case because it is not a requirement for aqueous humor to be emitted through device 4202 for system 4200 to be operational.

In some embodiments, an end of device 4202 extends external to the surface of eye 20 (as shown in FIG. 42). In some embodiments, an entirety of device 4202 is embedded below the surface of eye 20. In some embodiments, an end of device 4202 initially extends external to the surface of eye 20 but after time the sclera 6 and/or conjunctiva may grow over the end and an entirety of device 4202 is then effectively below the surface of eye 20.

In some embodiments, at least a portion 4204 of device 4202 includes a fluorescent dye that is reactive to the analyte being measured (e.g., reactive to glucose by means of a sensitive protein that relays the concentration by means of fluorescence). In some embodiments, an entirety of device 4202 includes the fluorescent dye. Examples of such fluorescent dyes include, but are not limited to, concanavalin A, glucose oxidase, glucose dehydrogenase and hexokinase/glucokinase, bacterial glucose-binding protein, and boronic acids derivatives (e.g., boronic acid functionalized fluorophores).

In some embodiments, the fluorescent dye is covalently bonded on the surface of device 4202 (partially or entirely). Alternatively, or additionally, in some embodiments the fluorescent dye is mixed in the pre-polymer that is used to fabricate device 4202.

The fluorescent dye will emit a particular color or fluorescence that correlates to an analyte concentration of the aqueous humor. In addition, the fluorescent dye will undergo a color change or fluorescence change in response to changes in the analyte concentration of the aqueous humor. Such color or fluorescence of the fluorescent dye of device 4202 can be detected and quantified by analysis system 4210.

Analysis system 4210 includes, at least, a detector 4212 that is in electrical communication with a processor 4214. Detector 4212 can detect the color or fluorescence of device 4202. Processor 4214 can receive signals from detector 4212 and determine an analyte concentration quantity associated with the color or fluorescence detected by detector 4212.

In some embodiments, analysis system 4210 is included in a device such as, but not limited to, a smart phone, eyeglasses, a remote device, and the like. In some embodiments, data from analysis system 4210 is wirelessly transmitted to an insulin pump and/or to a smart phone. In particular embodiments, an insulin pump is operated in a closed-loop fashion using wirelessly transmitted data from analysis system 4210 as feedback.

Figure 43:
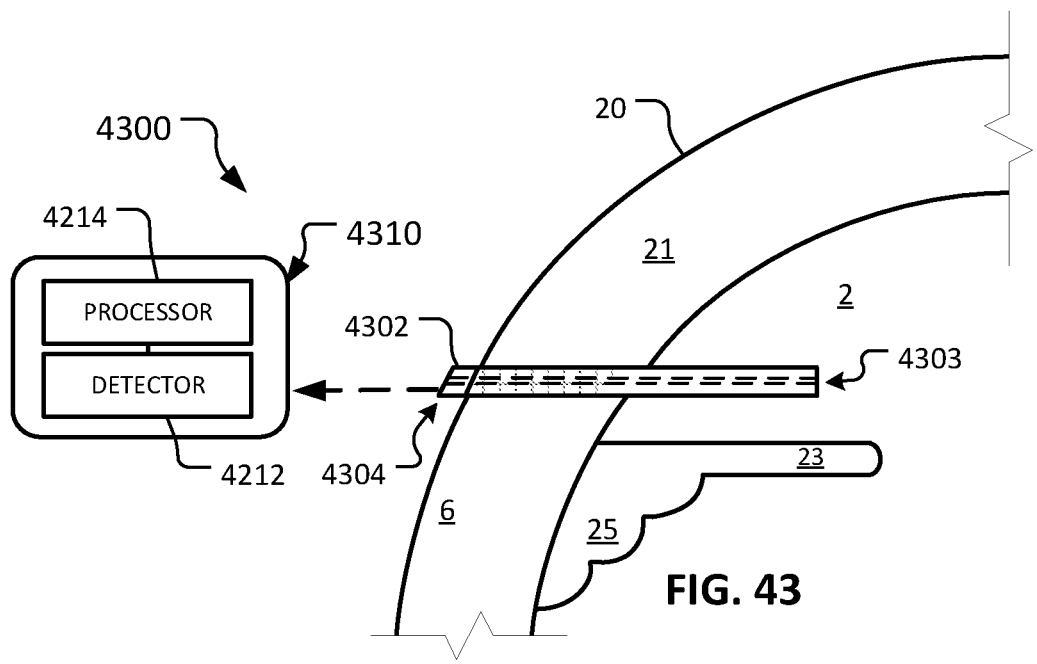
FIG. 43 is a sagittal cross-sectional schematic diagram of an eye that includes an example implanted device that has been adapted to indicate the presence of an analyte of aqueous humor being exuded through the device.

Referring to FIG. 43, system 4300 is another system for measuring analyte concentration in aqueous humor of an eye 20. For example, in one non-limiting example, system 4300 is used to measure glucose concentration in aqueous humor of eye 20. Other types of analytes can be additionally or alternatively measured using system 4300.

System 4300 includes a device 4302 and an analysis system 4310. Device 4302 can be similar to device 1 or any other implantable lumenal device described herein. Device 4302 includes a lumen 4303 as described elsewhere herein. Lumen 4303 provides a passage through which aqueous humor can be emitted through device 4302 to an external end 4304 of the device 4302 for system 4200 to be operational.

At least a portion of external end 4304 includes a fluorescent dye that is reactive to the analyte being measured. In some embodiments, only portions of external end 4304 that are not in constant contact with eye 20 include the fluorescent dye. Because lumen 4303 will transmit aqueous humor to the external end 4304, in some embodiments the fluorescent dye can be only on portions of device 4302 that are externally located in relation to eye 20. In some embodiments, an entirety of device 4302 includes the fluorescent dye.

In some embodiments, the fluorescent dye is covalently bonded on the surface of device 4302 (partially or entirely). Alternatively, or additionally, in some embodiments the fluorescent dye is mixed in the pre-polymer that is used to fabricate device 4302.

The fluorescent dye will emit a particular color or fluorescence that correlates to an analyte concentration of the aqueous humor. In addition, the fluorescent dye will undergo a color change or fluorescence change in response to changes in the analyte concentration of the aqueous humor. Such color or fluorescence of the fluorescent dye of device 4302 can be detected and quantified by analysis system 4310.

Analysis system 4310 includes, at least, a detector 4312 that is in electrical communication with a processor 4314. Detector 4312 can detect the color or fluorescence of device 4302. Processor 4314 can receive signals from detector 4312 and determine an analyte concentration quantity associated with the color or fluorescence detected by detector 4312.

In some embodiments, analysis system 4310 is included in a device such as, but not limited to, a smart phone, eyeglasses, a remote device, and the like. In some embodiments, data from analysis system 4310 is wirelessly transmitted to an insulin pump and/or to a smart phone. In particular embodiments, an insulin pump is operated in a closed-loop fashion using wirelessly transmitted data from analysis system 4310 as feedback.

Figure 44:
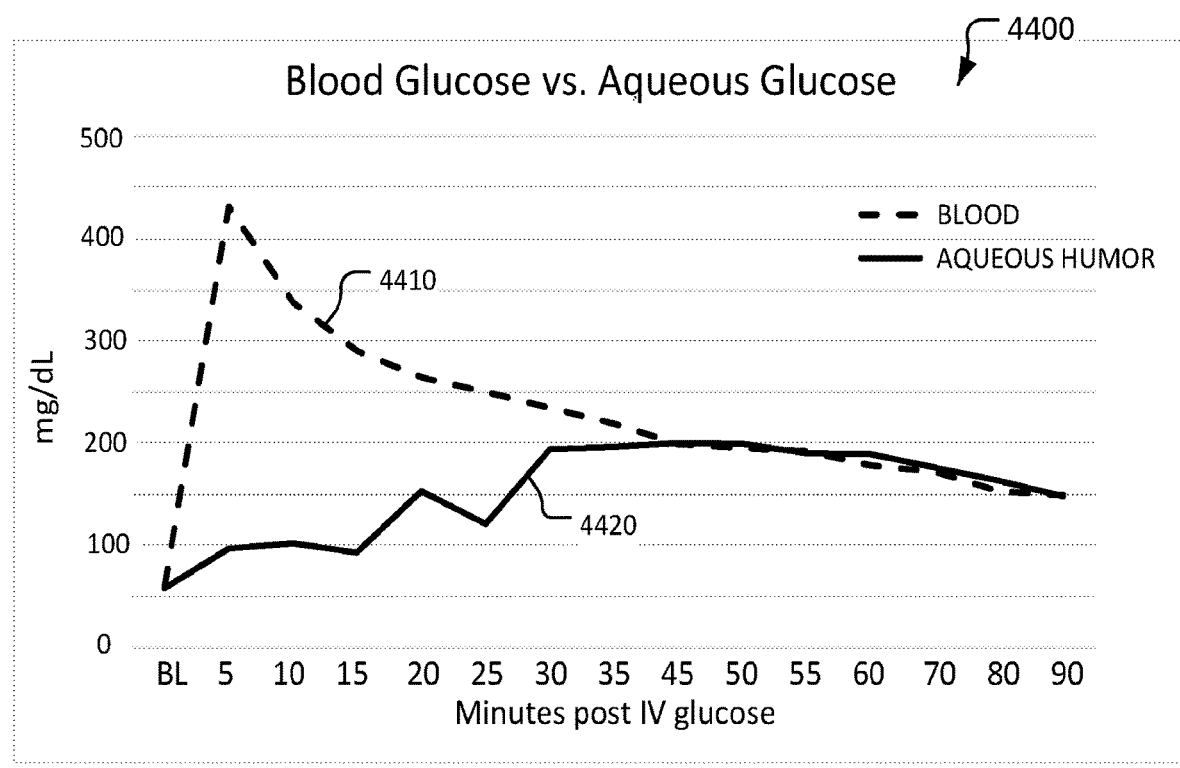
FIG. 44 is a time-based graph of glucose concentration data that was measured in the blood of a subject and in the aqueous humor of the subject.

Referring to FIG. 44, the inventors conducted a study to verify whether measurements of the glucose concentration of aqueous humor can be used as an indicator of the glucose concentration of blood. Graph 4400 is a time-based graph showing glucose concentration data that was measured in the blood of a subject (as indicated by dashed line 4410) and in the aqueous humor of the subject (as indicated by solid line 4420).

To perform this study, a female Yucatan "mini-pig" was anesthetize and a device (as described above) was implanted into the sclera of an eye of the animal to allow aqueous humor to flow from the anterior chamber of the eye through a lumen of the device and into the tear film. Three weeks after the surgery, the animal was once again anesthetized and an ear vein catheter and central venous line were put in place. Baseline blood glucose and aqueous humor glucose were assayed by simultaneously drawing samples of ear vein blood and aqueous humor (as transmitted by the device implanted in the eye) and assaying them for glucose concentrations with a point of care enzymatic based glucose analyzer. Simultaneous central line blood samples were also collected for analysis by an independent clinical chemistry lab and these results are not reported here but strongly correlated with the point of care assays.

The animal then received an intravenous bolus injection of 50% Dextrose (sugar) solution as described in a standard intravenous glucose tolerance test over the course of 1 minute. Simultaneously, samples of aqueous humor, ear vein blood, and central line blood were collected at regular intervals and assayed as previously described. The aqueous humor (line 4420) and ear vein blood (line 4410) glucose concentration values assayed with the point of care glucometer are plotted in graph 4400.

At baseline, pre bolus, and fasted starting time, graph 440 shows there is a strong agreement between aqueous humor and blood glucose levels. This could be expected because the low 180 MW glucose molecules easily equilibrate as an ultra filtrate of the blood into the aqueous humor.

During the extreme condition of a large bolus of glucose intravenously injected (as in the applied glucose tolerance test), the level of glucose in the blood (see line 4410) instantly peaks and slowly returns to baseline over the course of 1-2 hours depending on the normality of insulin response and the animals glycemic index (a test commonly used in medical practice to identify glycemic abnormalities and the potential disease of diabetes).

As shown by line 4420, this study showed a correlated rise in aqueous humor glucose concentration levels resulting from the large injection of glucose (while lagging behind the more responsive blood glucose concentration data of line 4410). This was to be expected as aqueous humor production is about 2-4 µl/minute in these animals, so the initial spiked ultra filtrates are initially diluted in the baseline anterior chamber aqueous humor of 0.5-1.0 cc volume.

While the initial blood glucose challenge is almost instantaneous, glucose resorption and metabolism is a slower process dependent on insulin production, distribution, binding, and cellular glucose metabolism. As such, once aqueous humor glucose concentration levels caught up with blood glucose levels at around 45 minutes as shown in graph 4400, both blood and aqueous humor glucose concentration levels returned towards baseline homeostasis levels at a similar rate and with quite striking similarity.

Based upon this, it is anticipated that a more natural "oral glucose tolerance test" (where the glucose is delivered in a bolus into an anesthetized animal's stomach and is absorbed into the blood stream in a more natural rate peaking at 30-60 minutes), will show that aqueous humor glucose concentration levels are very close to blood glucose concentration levels all the way up and back down. This process is expected to be similar to glucose homeostasis as seen and documented in other blood ultrafiltration such as subcutaneous interstitial fluid which is now commonly used for glucose monitoring with current closed loop insulin pumps and glucose sensors for diabetic patients.

This initial data (as depicted in graph 4400) supports the use of aqueous humor as a useful fluid to monitor patients glucose concentrations as a surrogate for blood glucose levels. It also demonstrates the utility of the implant devices described herein as tools to safely access aqueous humor for glucose monitoring.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings or described herein in a particular order, this should not be understood as requiring that such operations be performed in the particular order shown or in sequential order, or that all illustrated or described operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. As another example, systems 3700, 3800, and 3900 are described with respect to devices 1 and 3902, however systems 3700, 3800, and 3900 can instead include devices configured and shaped differently than as illustrated, such as including features of one or more of the other implantable devices described herein.

What is claimed is:

1. A system for monitoring a glucose concentration in aqueous humor, the system comprising:
    an implantable device configured to be surgically implanted in an eye and having a first end and a second end, the implantable device defining a lumen extending through the implantable device configured to transmit the aqueous humor from the first end positioned in an interior portion of the eye to an exterior portion of the second end positioned exterior of the eye;
    a light source configured to direct polarized light through the aqueous humor on the exterior portion of the second end; and
    a polarimeter configured for:
        receiving reflected polarized light that reflects from the exterior portion of the second end after passing through the aqueous humor on the exterior portion of the second end;
        detecting a polarity of the reflected polarized light; and
        determining the glucose concentration in the aqueous humor as a function of the detected polarity of the reflected polarized light.

2. The system of claim 1, wherein the lumen is configured to maintain a desired intraocular pressure for the treatment of glaucoma.

3. The system of claim 1, wherein the light source comprises a polarizer configured to direct the polarized light through the aqueous humor on the exterior portion of the implantable device.

4. The system of claim 3, wherein the system is configured to determine the glucose concentration in the aqueous humor without directing the polarized light into the eye.

5. A system for monitoring glucose concentration in aqueous humor, the system comprising:
    an implantable device configured to be surgically implanted in an eye;
    a sensor positioned on a portion of the implantable device that is positioned in aqueous humor of the eye when the implantable device is implanted in the eye;
    an analysis system configured for communication with the sensor and configured for processing data corresponding to the glucose concentration in the aqueous humor sensed by the sensor; and a set of eyeglasses that includes at least a portion of the analysis system,
wherein the implantable device defines a lumen extending through the implantable device, and
wherein the lumen is configured to transmit aqueous humor from an interior portion of the eye to an exterior of the eye when the implantable device is implanted in the eye.

6. The system of claim 5, wherein the implantable device and the analysis system each include an antenna for wirelessly communicating the data corresponding to the glucose concentration in the aqueous humor sensed by the sensor.

7. The system of claim 6, wherein the analysis system is configured for connecting to a mobile computing device.

8. A method for monitoring glucose concentration in aqueous humor, the method comprising:
inserting an implantable device into an eye, wherein the implantable device includes a first portion positioned in an interior portion of the eye and a second portion positioned exterior of the eye;
positioning the implantable device such that a glucose sensor on the implantable device is positioned proximate aqueous humor of the eye in the interior portion of the eye; and
providing a set of eyeglasses that includes at least a portion of an analysis system configured for communication with the glucose sensor and configured for processing data corresponding to the glucose concentration in the aqueous humor sensed by the glucose sensor.

9. The method of claim 8, wherein the implantable device has a lumen extending through the implantable device that is configured to transmit aqueous humor from the interior portion of the eye to the exterior of the eye.

10. The method of claim 8, wherein the analysis system is configured for connecting to a mobile computing device.

11. A method for determining a glucose concentration in aqueous humor, the method comprising:
providing light to a device implanted in an eye, wherein the device has a first end positioned in an interior portion of the eye and a second end positioned exterior of the eye, the device defining a lumen extending through the device between the first and second ends, the lumen transmitting the aqueous humor from the interior portion of the eye to an exterior portion of the second end positioned exterior of the eye;
passing the light through the aqueous humor that is on the exterior portion of the second end;
reflecting the light, by the exterior portion of the second end, to an optical detector that receives the reflected light; and
determining the glucose concentration in the aqueous humor as a function of the reflected light received by the optical detector.

12. The method of claim 11, wherein the light is a polarized beam of light projected from a light source having a polarizer, and wherein the glucose concentration is determined by a polarimeter using polarimetry.

13. The method of claim 12, wherein the method determines the glucose concentration in the aqueous humor without directing the polarized beam of into the eye.

14. A system for monitoring glucose concentration in aqueous humor, the system comprising:

an implantable device configured to be surgically implanted in an eye and defining a lumen extending through the implantable device configured to transmit aqueous humor from an interior portion of the eye to an exterior of the eye; and
a contact lens configured to be worn on the exterior of the eye, the contact lens defining a well configured for receiving the aqueous humor transmitted through the lumen to the exterior of the eye, the contact lens including a sensor coupled thereto, the sensor responsive to the glucose concentration of aqueous humor transmitted through the lumen to the well of the contact lens on the exterior of the eye.

15. The system of claim 14, wherein the contact lens further comprises an antenna for wirelessly transmitting signals from the sensor to an external device.

16. The system of claim 15, wherein the system includes the external device and the external device is one of a smart phone and an infusion pump.

17. The system of claim 14, wherein the sensor is an electrochemical sensor.

18. The system of claim 14, wherein the contact lens includes a ballast region that is more weighty than other portions of the contact lens.

19. The system of claim 14, wherein the well is a notch in a perimeter of the contact lens that is configured for receiving the aqueous humor transmitted through the lumen to the exterior of the eye.

20. The system of claim 19, wherein the contact lens includes a ballast region that is more weighty than other portions of the contact lens, and wherein the ballast region is on an opposite side of the contact lens in relation to the well.

21. A method for monitoring glucose concentration in aqueous humor, the method comprising:
implanting an implantable device in an eye, the implantable device defining a lumen extending through the implantable device configured to transmit aqueous humor from an interior portion of the eye to an exterior of the eye; and
providing a contact lens configured to be worn on the exterior of the eye, the contact lens defining a well configured for receiving the aqueous humor transmitted through the lumen to the exterior of the eye, the contact lens including a sensor coupled thereto, the sensor responsive to the glucose concentration of aqueous humor transmitted through the lumen to the well of the contact lens on the exterior of the eye.

22. The method of claim 21, wherein the well is a notch in a perimeter of the contact lens that is configured for receiving the aqueous humor transmitted through the lumen to the exterior of the eye.

23. The method of claim 22, wherein the contact lens includes a ballast region that is more weighty than other portions of the contact lens, and wherein the ballast region is on an opposite side of the contact lens in relation to the well.

24. The method of claim 23, the ballast region orients the well in alignment below an exterior end of the implantable device so that the aqueous humor transmitted to the exterior of the eye will tend to collect in well.

* * * * *